US011504351B2

(12) United States Patent
Dischler

(10) Patent No.: US 11,504,351 B2
(45) Date of Patent: *Nov. 22, 2022

(54) METHODS FOR RESTORING STEM CELL POOLS AND REDUCING EPIGENETIC AGE

(71) Applicant: Louis Dischler, Spartanburg, SC (US)

(72) Inventor: Louis Dischler, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/543,812

(22) Filed: Dec. 7, 2021

(65) Prior Publication Data

US 2022/0257558 A1 Aug. 18, 2022

Related U.S. Application Data

(62) Division of application No. 17/176,305, filed on Feb. 16, 2021, now Pat. No. 11,344,528.

(51) Int. Cl.
*A61K 31/352* (2006.01)
*A61K 45/06* (2006.01)
*A61K 31/20* (2006.01)
*A61K 31/26* (2006.01)

(52) U.S. Cl.
CPC ............ *A61K 31/352* (2013.01); *A61K 31/20* (2013.01); *A61K 31/26* (2013.01); *A61K 45/06* (2013.01)

(58) Field of Classification Search
CPC combination set(s) only.
See application file for complete search history.

(56) References Cited

U.S. PATENT DOCUMENTS

| 9,682,150 | B1 | 6/2017 | Gitterle et al. |
| 10,016,509 | B1 | 7/2018 | Elliott et al. |
| 2014/0140985 | A1 | 5/2014 | Moussa et al. |
| 2014/0221319 | A1 | 8/2014 | Sinclair et al. |
| 2018/0271906 | A1 | 9/2018 | Moussa et al. |
| 2019/0093075 | A1 | 3/2019 | Ratajczak et al. |

OTHER PUBLICATIONS

Börger et al., "Mesenchymal Stem/Stromal Cell-Derived Extracellular Vesicles and Their Potential as Novel Immunomodulatory Therapeutic Agents" International Journal of Molecular Science (Jul. 2017) PMID: 28684664, pp. 2-3.
Cataldo, "Chapter 13: Medicinal Chemistry and Pharmacological Potential of Fullerenes and Carbon Nanotubes" Springer (2008), pp. 317-334.
Cheng et al., "Sonic Hedgehog Signaling Mediates Resveratrol to Increase Proliferation of Neural Stem Cells After Oxygen-Glucose Deprivation/Reoxygenation Injury in Vitro," Cellular Physiology and Biochemistry (Mar. 2015), p. 2020.
Chistyakov et al., "Possible mechanisms of fullerene C antioxidant action" Biomed Research International (Oct. 2013) PMID: 24222918, p. 3.
Edmond, "Essential polyunsaturated fatty acids and the barrier to the brain: the components of a model for transport" Journal of Molecular Neuroscience (Apr.-Jun. 2001) PMID: 11478373, pp. 186, 190.
Grymula et al., "Evidence that the population of quiescent bone marrow-residing very small embryonic/epiblast-like stem cells (VSELs) expands in response to neurotoxic treatment" Journal of Cellular and Molecular Medicine (Sep. 2014) PMID: 24895014, p. 1803.
Gurveev et al., "β-Guanidinopropionic Acid Stimulates Brain Mitochondria Biogenesis and Alters Cognitive Behavior in Nondiseased Mid-Age Mice," Journal of Experimental Neuroscience (Apr. 2018) PMID: 29636631, p. 6.
Hao et al., "Fullerene mediates proliferation and cardiomyogenic differentiation of adipose-derived stem cells via modulation of MAPK pathway and cardiac protein expression" International Journal of Nanomedicine (Jan. 2016) PMID: 26848263, p. 269.
Higuera et al., "Patterns of amino acid metabolism by proliferating human mesenchymal stem cells" Tissue Engineering part A (Mar. 2012) PMID: 21943055, p. 660.
Hovarth, "DNA methylation age of human tissues and cell types" Genome Biology (May 2015) PMID: 24138928, pp. 12-13.
Huang et al., "Taurine enhances mouse cochlear neural stem cells proliferation and differentiation to sprial gangli through activating sonic hedgehog signaling pathway," Organogenesis (2018), p. 148.
Huang et al., "Dihydromyricetin Attenuates Dexamethasone-Induced Muscle Atrophy by Improving Mitochondrial Function via the PGC-1α Pathway," Cellular Physiology and Biochemistry (Aug. 2018) PMID: 30165349, p. 773.
Jang et al., "Nicotinamide-induced mitophagy: event mediated by high NAD+/NADH ratio and SIRT1 protein activation" Journal of Biological Chemistry (Jun. 2012) PMID: 22493485, pp. 19304-19307.
Khacho et al., "Mitochondrial Dynamics Impacts Stem Cell Identity and Fate Decisions by Regulating a Nuclear Transcriptional Program" Cell Stem Cell (Aug. 2016) PMID: 27237737, p. 245.
Khdour, "Phenothiazine antioxidants increase mitochondrial biogenesis and frataxin levels in Friedreich's ataxia cells," Medchemcomm (Jul. 2018) PMID: 30288223, p. 1495.
Kilberg et al., "Influence of Amino Acid Metabolism on Embryonic Stem Cell Function and Differentiation," Advances in Nutrition Jul. 2016) PMID: 27422515, p. 785S.
Klimova, "Nicotinamide mononucleotide alters mitochondrial dynamics by SIRT3-dependent mechanism in male mice" Journal of Neuroscience Research (Aug. 2019) PMID: 30801823, p. 1.
Knoblich, "Mechanisms of asymmetric stem cell division," Cell (Feb. 2008) PMID: 18295577, pp. 583-585.
Kornasio et al., "βhydroxy-β-methylbutyrate (HMB) stimulates myogenic cell proliferation, differentiation and survival via the MAPK/ERK and PI3K/Akt pathways," Biochimica et Biophysica Acta (BBA)—Molecular Cell Research (May 2009) PMID: 19211028, pp. 755-757.
Lee et al., "Methionine restriction and life-span control" (Jan. 2016) Ann N Y Acad Sci PMID: 26663138, p. 1.

(Continued)

*Primary Examiner* — Kathrien A Hartsfield

(57) ABSTRACT

Disclosed are methods and compositions for reducing the epigenetic age of organisms, especially that of adult humans, which provide for proliferating endogenous stem cells, removing aberrant epigenetic marks from chromosomes and mitochondrial DNA, and replacement of senescent cells.

20 Claims, 6 Drawing Sheets

(56) References Cited

OTHER PUBLICATIONS

Liu et al., "Dihydromyricetin: A review on identification and quantification methods, biological activities, chemical stability, metabolism and approaches to enhance its bioavailability," Trends in Food Science & Technology (Sep. 2019) PMID: 32288229, p. 591.

Nohara et al., "The important role of caspase-10 in sodium butyrate-induced apoptosis," The Kobe journal of medical science (2017) PMID: 18204303, pp. 265-266.

O'Mealey et al., "Sulforaphane is a Nrf2-independent inhibitor of mitochondrial fission," Redox Biology (Apr. 2017) PMID: 27889639, p. 104.

Oz et al., "Methylene blue and Alzheimer's disease," Biochemical Pharmacology (May 2009) PMID: 19433072, p. 929.

Saini, et al., "DNA Methyltransferase1 (DNMT1) Isoform3 methylates mitochondrial genome and modulates its biology" Scientific Reports (May 2017) PMID: 28484249, pp. 5-6.

Senyilmaz et al., "Regulation of mitochondrial morphology and function by Stearoylation of TfR1," Nature (Sep. 2015) PMID: 26214738, p. 1.

Shiraki et al., "Methionine metabolism regulates maintenance and differentiation of human pluripotent stem cells," Cell Metabolism (May 2014) PMID: 24746804, p. 789.

Venkei et al., "Emerging mechanisms of asymmetric stem cell division," Journal of Cell Biology (Nov. 2018) PMID: 30232100, pp. 3791-3792.

Weidner et al., "Aging of blood can be tracked by DNA methylation changes at just three CpG sites," Genome Biology (Feb. 2014) PMID: 24490752, p. 8.

Xavier et al., "Tauroursodeoxycholic acid increases neural stem cell pool and neuronal conversion by regulating mitochondria-cell cycle retrograde signaling," (Nov. 2014) PMID: 25483094, p. 3576, 3583.

Yang et al., "Antioxidative fullerol promotes osteogenesis of human adipose-derived stem cells," International Journal of Nanomedicine (Aug. 2014) PMID: 25187705, p. 4023.

Zhang et al., "The role of mitochondria in stem cell fate and aging," Development (Apr. 2018) PMID: 29654217, pp. 1-2.

METHODS FOR RESTORING STEM CELL POOLS AND REDUCING EPIGENETIC AGE

CROSS-REFERENCE TO RELATED APPLICATIONS

This application is a division of co-pending application Ser. No. 17/176,305, filed on 16 Feb. 2021, which claimed benefit of provisional Application No. 62/980,501 filed on 24 Feb. 2020, and provisional Application No. 63/136,662 filed on 13 Jan. 2021, and is a continuation-in-part of co-pending application Ser. No. 16/540,200 filed 14 Aug. 2019, which claimed benefit of provisional Application No. 62/719,637 filed on 18 Aug. 2018, with the contents of each of the above-listed applications hereby incorporated by reference in their entireties, and which are not considered to be prior art with respect to the present invention.

The claimed methods and antiaging compositions primarily relate to the rapid reduction of average epigenetic age of an adult human organism and tissues thereof, the expansion of stem cell pools, the restoration of mitochondrial health and the restoration of more youthful function.

BACKGROUND OF THE INVENTION

Numerous putative sources of aging are known. These include mutations of nuclear and mitochondrial DNA, inflammation, glycative cross-linking, the intra and extra cellular accumulation of indigestible materials such as lipofuscin, Aβ and P-tau in the brain and the associated decline in memory, musculoskeletal disorders, and the oxidized cholesterol derivatives in atherosclerotic plaques. These contribute to the aging of the entire organism or substantial parts thereof, and many believe that so many disparate sources of aging interact that aging is inevitable.

The shortening of telomeres is often considered another source of aging, but herein is considered to be a calendar or clock that provides cellular expiration dates for an organism that is constantly renewing itself. Without stem cells to replace somatic cells reaching their expiration dates, the organism would enter a Hayflick crisis and die. The Hayflick limit is the number of times somatic cells can divide before reaching senescence, typically 40 to 70 divisions. As this limit is due to the shortening of telomeres, one currently popular solution to the problem is to extend telomeres with supplements such as astragalus extracts containing cycloastragenol. While this may provide short-term health benefits by delaying the Hayflick crisis, it allows cells to continue aging epigenetically, thus becoming ever more dysfunctional.

Epigenetics is the study of the meta programing that controls the expression of genes, wherein hundreds of human cell types are programed from selected portions of the underlying nuclear DNA (nDNA) that is otherwise identical for all diploid cells. Nuclear DNA is bound to proteins called histones, and the expression of genes is raised or lowered by histone modifications and nDNA methylation. Histones are primarily modified by methylation, but also by phosphorylation, acetylation, ubiquitylation, and sumoylation. At least eleven types of modifications are presently known. These modifications form the epigenome—the epigenetic code that lies above the nDNA code and modulates its expression. Errors in the epigenome—epimutations that occur far more frequently than mutations in the underlying nDNA it controls—degrade the proper functioning of cells and result in aging. In addition, somatic cells become senescent (suffering irreversible cell cycle arrest) due to telomeric shortening, nDNA mutations and other damage. Even a small percentage of senescent cells are known to have an outsized negative effect on the organism. They create inflammation and can drive neighboring cells into senescence with chemical signals, referred to as the senescence-associated secretory phenotype (SASP). While the body removes senescent cells naturally by apoptosis, with age the number of cells reaching senescence steadily increases while stem cell pools decline and the natural processes of clearance and replacement fail to keep up, beginning a vicious cycle wherein epigenetically old senescent cells accumulate at an accelerating rate.

Epimutations also occur in the nDNA of stem cells, and are propagated thereby to their progeny by methyltransferases. Just as nDNA picks up aberrant methylation marks, so does mitochondrial DNA (mtDNA). These marks are similarly transferred by methyltransferase and thus are persistent. They may be inherited or added stochastically, or by environmental conditions such as air quality and nutrition. In 2017, Saini, et al. reported that DNA Methyltransferase1 (DNMT1) isoform3 methylates the mitochondrial genome. Ultimately mtDNA can become hypermethylated and dysfunctional, with reduced ATP production.

Methods and supplements for reducing mtDNA methylation would thus increase ATP and athletic performance, improve organ health, and reduce the severity of many diseases of aging.

The least methylated nDNA are found in stem cells. The human organism has stem cells of several types, with variable potential growth possibilities. During fetal development, totipotent stem cells possess the ability to differentiate into any cell of the body and the placenta. Those disappear after a few cycles of replication, leaving the developing fetus with pluripotent (embryonic) stem cells that can develop into any cell of the body, and finally multipotent (adult) stem cells that have more epigenetic nDNA programing than totipotent or pluripotent cells and thus a reduced ability to differentiate into any cell type. Residual pluripotent stem cells in the adult have recently been discovered. All of these, along with more specialized stem cells like satellite cells are herein collectively called stem cells (SCs) unless otherwise specified, while diploid cells with nDNA epigenetically programed to perform as any of the more than two hundred cell types in the body are called somatic cells.

Stem cells are present in all or nearly all tissues of the mature organism. With aging, however, the active SC populations fall even while the function of somatic cells is degraded by stochastic changes to the epigenome (epimutations) which occur at a rate many times the mutation rate of the underlying nDNA, thus detuning somatic cells for their specific function. The result is ageing and the myriad dysfunctions that entails. History is replete with attempts to turn back the clock, with the earliest written records dating back at least to the Epic of Gilgamesh in 1,800 BC, wherein the apocryphal Gilgamesh finds and loses a plant that is said to restore youth. While no single substance is known that can reverse the biological clock, the present application discloses methods and antiaging compositions for doing just that.

According to a current hypothesis, damage to the epigenetic code is the main cause of aging. Methyl groups define most of the epigenetic pattern, and mutations to this pattern occur relentlessly throughout life due to various environmental conditions and during mitosis. During replication of nuclear DNA (nDNA), the positions of methyl groups are transferred from the parent nDNA strand to the daughter strand by methyltransferases, which operate with relatively poor fidelity compared to the nDNA polymerases that replicates the underlying pattern of nDNA bases. Methylation errors result in an inappropriate genetic expression for a given cell type, thereby detuning cells for their assigned purpose and propagating this dysregulation to daughter cells, with the level of dysregulation increasing with each generation.

While the epimutations of most genes are stochastic, some portions of the epigenome have been found that degrade with such regularity that they can serve as an epigenetic clock. Selected methylation sites have been found where the aggregate methylation status correlates well with chronological age. Horvath's clock is one example, which uses several hundred sites. Weidner's clock is another that samples just 3 sites. The age obtained from such clocks reflects only an average age of cells from the body or selected tissues thereof, which generally comprises a mix of epigenetically old and young cells. During differentiation, stem cells take on an epigenetic pattern appropriate to a specific cell type with near zero age. Fetal somatic cells have a low epigenetic age that increases rapidly through childhood and then at a slower and generally linear fashion until death. Reversing the epigenetic age of an organism is thus a goal that many seek.

Pluripotent (embryonic) stem cells have recently been found to still exist in the adult. Such cells exist in bone marrow and may supply other tissues via blood circulation. In 2014, Grymula et al. reported that bone marrow provided a source of very small embryonic-like stem cells (VSELs), which can mobilize and circulate with blood. They proposed that these VSELs serve as a reserve of immortal pluripotent stem cells that can give rise to adult stem cells, thus refilling adult stem cell pools. VSELs apparently escaped discovery due to their exceedingly small size and failure of techniques then in use to properly extract them.

Declining numbers of VSELs are associated with aging. In U.S. Patent Application No. 20190093075, Ratajczak et al. claimed a method of expanding VSELs ex vivo, but a simple method of expanding VSELs and other SCs in vivo would be far more desirable.

Stem cells secrete extracellular vesicles that create an environment allowing endogenous stem and progenitor cells to successfully repair damaged tissues, thus expanding stem cell pools would have more than one mode of action in restoring health. This active area of research was reviewed by Börger et al. in 2017.

Paracrine factors modulate the behavior of stem cells. In 2018, Huang et al. reported that taurine enhanced neural SC proliferation through a sonic hedgehog signaling pathway, and in 2015 Cheng et al. reported that resveratrol enhanced neural SC proliferation after injury, also through a sonic hedgehog signaling pathway.

The replication of stem cells is orchestrated in part by their mitochondria. Mitochondria are organelles of ancient bacterial origin that provide energy for cells by a series of oxidation-reduction reactions, degrading fatty acids, amino acids, and pyruvate (from glucose) to produce ATP, which is then used by cells as their primary energy source. Mitochondria are present in all human cells except red blood cells. The numbers per cell vary according to the energy needs of particular cell types, but the average cell comprises a thousand or more. The mitochondrial count is in constant flux as mitochondria continuously fission and fuse to form individual units or interconnected thread-like structures within cells. Each mitochondrion typically contains multiple copies of bacterial style DNA loops (mtDNA) that operate outside the nDNA system, but with a good deal of crosstalk. In healthy cells, there is an equilibrium between fission and fusion that serves to mix mitochondrial content during fusion and isolate defective mtDNA during fission so they can be lysosomally degraded. Mitochondrial morphology also serves as a switch for cellular processes. In 2016, Khacho et al. hypothesized that an overall fusion state biases stem cells into symmetric proliferation (self-renewal), producing two daughter stem cells, while a fission state biases stem cells into asymmetric differentiation where one daughter cell remains a stem cell and the other becomes a somatic cell. Without intervention, it has been estimated that more than 80% of stem cell replication is asymmetric.

In 2015, Senyilmaz et al. reported that increased stearic acid (C18:0) intake boosted mitochondrial fusion in flies. In 2017, O'Mealey et al. reported that sulforaphane caused mitochondrial hyperfusion in cultured cells. According to Edmond in 2001, common saturated and monounsaturated fatty acids such as stearic and oleic acids do not enter the brain parenchyma, whereas polyunsaturated fatty acids such as EPA and DHA do. Stearic acid is thus blocked by the blood brain barrier (BBB), while sulforaphane is not. In 2018, Huang et al. reported that dihydromyricetin promotes mitochondria fusion and biogenesis, and in 2019, Liu et al. reported that dihydromyricetin crosses the BBB and is generally eliminated from the body in about 12 hours.

In 2012, Jang et al. showed that a high ratio of oxidized to reduced nicotinamide adenine dinucleotide ($NAD^+$/NADH) promotes mitochondrial fission, thus increasing $NAD^+$ will raise that ratio. While the mitochondria of most cells become fragmented in the presence of high $NAD^+$/NADH ratio, neural cell mitochondria respond anomalously. According to Klimova in Aug. 2019, neurons have a much higher expression of SIRT3, which when stimulated by $NAD^+$ precursor NMN, reduce mitochondrial fragmentation.

In 2018, Venkei et al. noted that the mitochondria of dividing stem cells become segregated, with the most dysfunctional mitochondria going to the somatic daughter cells where they can be removed by quality control processes. It is hypothesized herein that mitochondrial fusion prevents this segregation and thereby suppresses asymmetric replication. This would be a direct effect rather than the indirect effect of suppression of ROS via mitochondrial fusion postulated by Khacho et al., who suggested that elongated mitochondria reduce ROS in neural stem cells (NSCs), thereby promoting symmetric division. In 2008, Knoblich taught that Drosophila stem cells in contact with other stem cells in a niche primarily replicate asymmetrically. In the elderly, much of the stem cell population in a niche may be senescent or have impaired regenerative capacity, thus a method of overriding asymmetric replication resulting from the presence of neighboring stem cells in a niche would allow the SC pool to be expanded.

Mitochondria are energy producing organelles having inner and outer membranes with numerous pores that allow metabolites and ions to pass in a controlled fashion while creating a proton gradient across the inner membrane that can be likened to a battery or capacitor that employs protons instead of electrons. The return flow of protons across the inner membrane is used to produce adenosine triphosphate (ATP) by the process of oxidative phosphorylation. It is known in the art that mitochondria of stem cells are kept quiescent by channels that allow the proton gradient to discharge without doing useful work, thereby preventing ATP production in favor of glycolysis, which is considerably less efficient. Such channels are created by uncoupling proteins (UCP), commonly numbered UCP1, UCP2, etc., in the order of discovery. Five homologues are known in mammals. The mitochondria of human stem cells have numerous channels formed of three UCP2 molecules joined around an axis that allow a return flow of protons ($H^+$) through the inner membrane of mitochondria. This proton leakage maintains SC quiescence and limits reactive oxygen species (ROS) production. In 2011, Zhang et al. showed that UCP2 expression was up to ten times higher in human pluripotent stem cells than in human fibroblasts. They found that UCP2 was repressed during differentiation, by unknown means.

While the exact geometry and manner of activity of UPC2 channels is not well understood, NMR studies suggest that three molecules are joined along an axis to produce a passageway therebetween that diverges slightly at the distal ends.

The use of fullerenes to prolong life was the subject of U.S. Patent Applications Nos. 20140140985 and 20180271906 by Moussa et al. It was believed by the inventors that $C_{60}$ dissolved in oil scavenged free radicals to prolong the life of rats. This discovery resulted in several companies beginning to sell this product online. And while some users did experience positive results, these tended to fade with time, and after years of use, some complained that they were worse off than before. It is suggested herein that stimulating stem cell mitochondria with $C_{60}$ without controlling mitochondrial morphology or considering stem cell nutrition will ultimately result in asymmetric differentiation, cell cycle arrest, and depletion of stem cell pools, potentially producing a decrease in human longevity rather than an increase. Moussa's rats did not live long enough or receive enough treatments to experience this issue, but those versed in the art recognize that the depletion of functional stem cells is a major source of human aging.

U.S. Pat. No. 9,682,150 to Gitterle et al. and U.S. Pat. No. 10,016,509 to Elliott et al. were directed to combinations of $C_{60}$ with phytonutrients and antioxidants mixed into oils, but neither appreciated that fullerenes can be used to restore stem cell pools. Neither appreciated that fullerenes could be used to reduce epigenetic age.

In 2014, Yang et al. showed that the water soluble polyhydroxylated fullerene (fullerol) stimulated osteogenic differentiation of human adipose-derived stem cells, while in 2016, Hao et al. found that C60 stimulated brown adipose-derived stem cells. Neither appreciated the mechanism or that fullerenes could be used to restore stem cell pools.

For C60 dissolved in olive oil, concentrations less than 1 mg/ml are achieved at room temperature. Much higher concentrations can be obtained in oils and fatty acids by heating to a temperature substantially above room temperature, as discussed by Cataldo in 2008.

According to theoretical work by Chistyakov et al. in 2013, C60 can absorb protons and thus become charged.

A number of $NAD^+$ supplements are discussed by Horn in U.S. Patent Application No. 20180071273. While increasing $NAD^+$ tends to increase mitochondrial fission in most cell types, according to Klimova in 2019, the $NAD^+$ precursor NMN drives neural mitochondria to fusion via a SIRT3 mechanism. Other SIRT3 promoters are known, such as pyrroloquinoline quinone (PQQ), methylene blue (MB), alpha lipoic acid (ALA), and Tauroursodeoxycholic acid (TUDCA), all of which are known to promote mitochondrial biogenesis. In 2018, Khdour et al. disclosed a number of MB derivatives that enhance mitochondrial biogenesis.

An interrelated source of cellular aging derives from telomeres. Telomeres shorten and otherwise degrade with age due to attack by ROS and erosion during mitosis. Stem cells produce the enzyme telomerase for restoring telomeric length, but most somatic cells substantially lack this enzyme and thus their ability to replicate fails as the number of replications reaches the Hayflick limit. At this point somatic cells cease dividing and become senescent. While the shortening of telomeres is considered a source of aging by some, it has at least two advantages for the adult human organism: first, it halts the proliferation of tumor cells that do not produce telomerase, and second, it halts the replication of epigenetically old cells that would otherwise populate the organism with cells detuned for their tasks by ever growing numbers of epimutations. Thus rescuing near-senescent cells by lengthening telomers can lower telomeric age while detrimentally increasing epigenetic age. It has been found during the present work that use of telomerase supplements can increase epigenetic age rapidly, as old cells no longer become senescent and thus continue to age epigenetically. While in the short term a user might see health benefits due to the reduced load of senescent cells, this will be a temporary improvement.

Senescent cells can be driven into apoptosis with senolytic substances. In 2017, Zhu et al. discussed a number of senolytic compounds capable of increasing the natural removal of senescence cells via apoptosis. These include dasatinib, quercetin, navitoclax, piperlongumine, and fisetin.

Some adult stem cells are known to require a specific group of nutrients, but it is likely that the nutritional requirements of all stem cell pools are not yet known. In 2014, Kilberg et al. reported that the amino acid requirements of human embryonic cells (hESCs) in vitro included methionine, lysine and leucine. Absent these amino acids, hESCs entered cell arrest and ultimately progressed to apoptosis. In 2014, Shiraki et al. showed that depletion of either methionine or SAMe reduces proliferation and can result in prolonged cell arrest of pluripotent cells leading to apoptosis.

The level of methionine in the diet is associated with shortened lifespan, and the currently popular calorie restriction diet for longevity has been said to actually amount to methionine restriction. In 2016, Lee et al. listed a number of pathways whereby methionine restriction might extend lifespan, yet the results are inconsistent and thus unconvincing.

SC nutritional requirements have been found to vary. In 2012, Higuera et al. studied the uptake by mesenchymal stem cells of various amino acids and found that the amounts used varied widely according to conditions—whether growing statically on plates or dynamically in a bioreactor, for instance. For a dynamic culture, glutamine, leucine and isoleucine were most used.

It is known by those versed in the art that stem cells may be removed from an organism, stimulated in vitro, then returned to the same organism or to a different one—called autologous or allogeneic transplantation, respectively. Such procedures are difficult, dangerous and expensive. While appropriate in certain instances, such as when bone marrow has been destroyed by chemotherapy, they are not appropriate for general epigenetic age reversal, thus the ancient desire to turn back the clock has remained unmet, until now.

ABBREVIATIONS

ALA Alpha lipoic acid
AKG alpha-ketoglutarate
ATP Adenosine triphosphate
BBB Blood Brain Barrier
DHA Docosahexaenoic acid DHEA Dehydroepiandrosterone
DHM Dihydromyricetin
EPA Eicosapentaenoic acid
FFA Free fatty acid
GH Growth hormone
GMS Glycerol monostearate
MCT Medium chain triglycerides
MB Methylene blue
MS1 Mitochondrial switch 1
MS2 Mitochondrial switch 2
MSC Mesenchymal-like stem cell
mtDNA Mitochondrial DNA
NAD Nicotinamide adenine dinucleotide
NAM Nicotinamide
NAM+R Nicotinamide plus ribose
nDNA Nuclear DNA
NMN Nicotinamide mononucleotide
NMR Nuclear magnetic resonance
NSC Neural stem cells
PQQ Pyrroloquinoline quinone
rRNA Ribosomal RNA
ROS Reactive oxygen species
SASP Senescence-associated secretory phenotype
SC Stem cell
Shh Sonic hedgehog
SIRT3 Sirtuin-3, a NAD-dependent deacetylase
TAC Transit amplifying cell
TET Ten-eleven translocation (a type of demethylation enzyme)
tRNA Transfer RNA
UCP2 Uncoupling protein 2
VSEL Very small embryonic-like stem cell
β-GPA β-Guanidinopropionic acid
ΔΨm Mitochondrial membrane potential

SUMMARY OF THE INVENTION

The disclosed protocols and antiaging supplements provide for expanding stem cell numbers while reducing the epigenetic age of nDNA, and reducing mtDNA dysfunction of a mammalian organism, especially an adult human subject, and most especially a subject of geriatric age. Age reversal of years per month and mitochondrial dysfunction reversal in a matter of weeks is possible.

In one embodiment of the invention, epigenetic age is lowered by first restoring stem cell (SC) pools to a more youthful condition in vivo. SC populations are expanded by self-renewal during which aberrant epigenetic marks are removed from DNA and associated histones, followed by in vivo replacement of senescent cells with differentiated SCs.

Stem cells are manipulated with two mitochondrial switches. The first switch is the modification of mitochondrial morphology to fusion, the second is the restoration of ATP production. Properly set, these switches promote self-renewal and refill stem cell niches.

Setting the first mitochondrial switch (MS1) to fusion biases SCs to symmetric division (self-renewal). Setting the second mitochondrial switch (MS2) by blocking UCP2 pores of SC mitochondria restores ATP production. Applying the first and second switches drive self-renewal.

MS1 is activated by administering therapeutically effective doses of mitochondrial fusion promoters. Nonlimiting examples are stearic acid and/or sulforaphane, or sources thereof.

MS2 is activated by administering therapeutically effective doses of UCP2 pore blockers, thus restoring ATP production and banishing quiescence. UCP2 pore blockers include fullerenes and fullerene derivatives, and the C60 fullerene in particular. C60 is preferred as it is known to be non-toxic, and has a predilection for mitochondria.

Epigenetic age may be further lowered during self-renewal by administering supplements to promote natural enzymes such as demethylases and deacetylases that remove aberrant epigenetic marks from nDNA and associated histones.

Demethylases can be promoted by oral supplementation with ketoglutarates. Nonlimiting examples of ketoglutarate compounds useful in the instant invention include alpha-ketoglutarate, ammonium alpha-ketoglutarate, arginine alpha-ketoglutarate, calcium alpha-ketoglutarate, creatine alpha-ketoglutarate, glutamine alpha-ketoglutarate, leucine alpha-ketoglutarate, lithium alpha-ketoglutarate, magnesium alpha-ketoglutarate, ornithine alpha-ketoglutarate, potassium alpha-ketoglutarate, sodium alpha-ketoglutarate, and taurine alpha-ketoglutarate. Demethylase activity depends in part on the availability of alpha-ketoglutarate, which is an intermediate in the Krebs cycle. The derivatives may be used at dosages twice that of alpha-ketoglutarate, due to higher molecular weight and slower rates of absorption.

In another embodiment of the invention, demethylase promoters are used to remove epigenetic marks from mtDNA during biogenesis of mitochondria, whereby replicated mtDNA loops have reduced methylation and increased ATP production. For maximizing ATP production, MS1 is set to either fission or fusion, and a demethylase promoter is administered, such as alpha-ketoglutaric acid or a pharmaceutically acceptable derivative thereof, along with a biogenesis promoter. Alternating MS1 between fusion and fission in the presence of demethylase and biogenesis promoters rapidly reduces mitochondrial dysfunction due to hypermethylation and genetic mutations of mtDNA.

A preferred biogenesis promoter is pyrroloquinoline quinone (PQQ). Other known biogenesis promoters include methylthioninium chloride (methylene blue, MB). The promoters of fusion, demethylase and biogenesis can be administered to an organism by any pharmaceutically acceptable route, but preferrable orally.

A useful antiaging composition for cleaning up aberrant methylation of mtDNA comprises a biogenesis promoter, a demethylase promoter, and a fusion or fission promoter in an oral dose. An exemplary composition using fusion comprises glycerol monostearate (GMS), pyrroloquinoline quinone (PQQ), and alpha-ketoglutarate (AKG). GMS and AKG are preferred due to their rapid absorption. An exemplary composition using fission comprises nicotinamide (NAM), PQQ, and AKG and/or other AKG derivatives. Nicotinamide and AKG are preferred due to rapid absorption. Nicotinamide with ribose is even more effective for fission, and is also rapidly absorbed. Nicotinic acid (niacin) is an alternative to nicotinamide. It may be used alone, or with ribose, and may also be used with nicotinamide, and with nicotinamide and ribose. Doses of either fission or fusion compositions are preferably delivered by oral means, and can be conveniently provided in tablet, capsule or powder form.

Administering cell nutrition during SC self-renewal or shortly thereafter has been found to be efficacious. SC nutrition during the following days is also desirable. It is known that SC niches are prevented from overfilling by either terminal differentiation or cell cycle arrest, and administering the correct nutrition biases this homeostatic process to differentiation and replacement of aged somatic cells. Fission promoters may also be used to promote senescent cell replacement, as fission promotes both SC differentiation and senescent cell apoptosis. It is desirable to allow sufficient time between self-renewal (using fusion) and senescent cell apoptosis and replacement (using fission) to allow for SC maturation. One day is generally sufficient.

It is thus a principle object of some aspects of the present invention to lower the levels of aberrant epigenetic marks on the chromosomes (nDNA plus associated histones) of an organism.

Another principle object of some aspects of the present invention is to proliferate endogenous stem cells in situ using mitochondrial switches.

Another principle object of some aspects of the present invention is to replace epigenetically old somatic cells with epigenetically young somatic cells derived from stem cells in restored stem cell pools, thereby reducing the average epigenetic age of the organism.

Another object of some aspects of the present invention is to lower cellular populations of genetically and epigenetically damaged mtDNA, thereby increasing ATP production.

These together with other objects of the invention and various novel features that characterize the invention are particularized in the claims that form part of this disclosure. For a better understanding of the invention, its advantages and the specific objects attained by its uses, reference should be made to the accompanying drawings and descriptive matter in which preferred embodiments of the invention are illustrated.

BRIEF DESCRIPTION OF THE DRAWINGS

The protocols and nutritive compositions will be better understood and objects other than those set forth above will become apparent when consideration is given to the following detailed descriptions thereof. Such descriptions reference the annexed drawings, wherein.

DETAILED DESCRIPTION OF THE INVENTION

Figure 1:
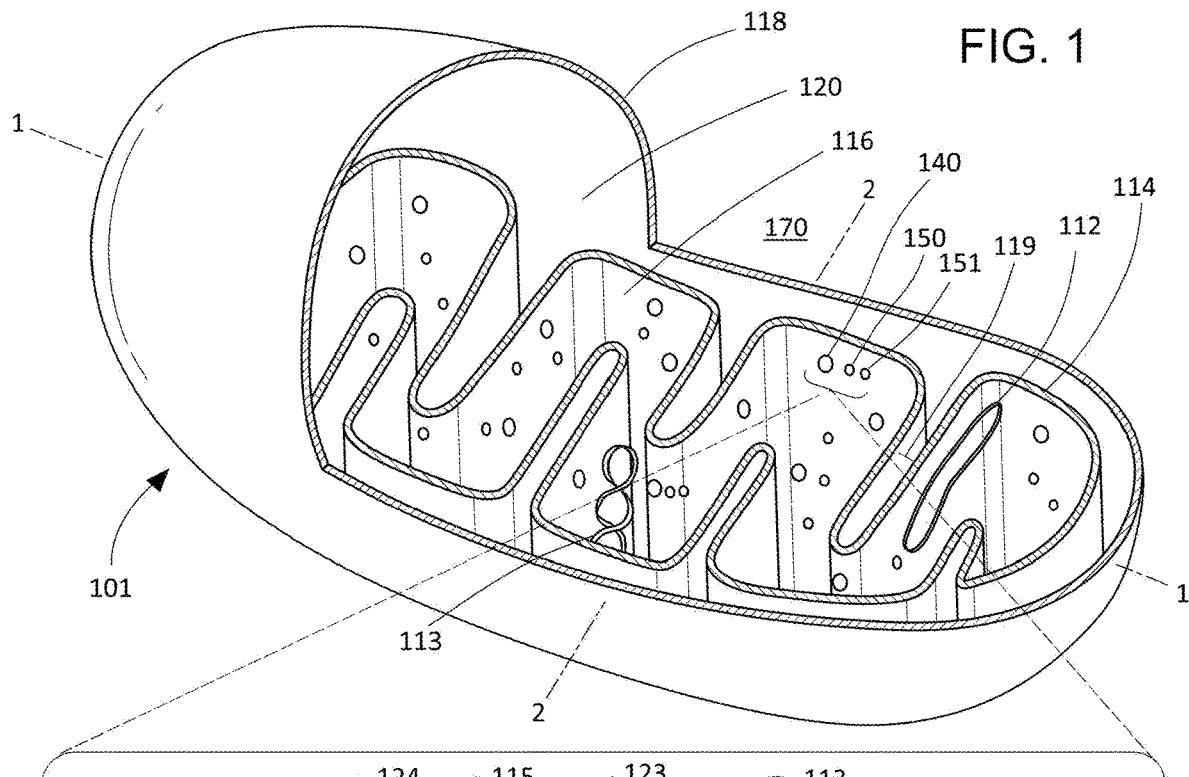
FIG. 1 is an idealized cutaway view of a typical mitochondrion in an intermediate state between fission and fusion.

It is herein argued that aging is primarily an extended Hayflick crisis wherein depleted stem cell pools are unable to replace growing numbers of cells reaching their telomeric expiration dates, resulting in the increasing epigenetic age of somatic cells and the buildup of senescent cells. By effectively managing this Hayflick crisis, aging can be stopped and reversed. Disclosed is a method for repeatedly stimulating the symmetric proliferation of endogenous stem cells to refill stem cell pools, followed by stimulating the apoptosis of senescent cells, whereby epigenetic age of the organism is reduced and a more youthful state restored.

Preexisting endogenous stem cells are preferred over exogenous stem cells as they are completely compatible with the organism and already distributed widely in tissues. However, endogenous stem cells are not present in sufficient numbers and/or activity to decrease epigenetic age naturally and their numbers decline with chronological age, deficiencies addressed by the methods and nutritive compositions disclosed herein.

MITOCHONDRIAL FUSION AND FISSION

Mitochondria play a central role in reversing aging. Two mitochondrial switches are used herein to control stem cell (SC) behavior. Mitochondrial switch 1 (MS1) can be set to either fission or fusion, while mitochondrial switch 2 (MS2) can be set to on or off. In the MS2 on state, SC mitochondria produce ATP, while in the MS2 off state, they produce none, or substantially none.

The following switch states are relevant to stem cells:
MS1 fusion
MS2 on
Result: SCs divide symmetrically (proliferation)
MS1 fission
MS2 on
Result: SCs divide asymmetrically (differentiation)
MS1 fission, fusion, or intermediate
MS2 off
Result: SCs are quiescent Most commonly for SCs, MS1 is intermediate and MS2 is off.

Proliferation (self-renewal) of stem cells is achieved by first administering a mitochondrial fusion promoter (setting MS1 to fusion), then administering a mitochondrial stimulant that blocks proton channels created by mitochondrial uncoupling proteins (UCP2s), or otherwise increases ATP output of SC mitochondria sufficiently to banish quiescence (setting MS2 to on). Proliferation, where one SC becomes two SC daughters, results in expansion of SC pools.

By replacing epigenetically old senescent cells with epigenetically young cells derived from enlarged SC pools, the epigenetic age of the organism can be reduced at many times the rate of chronological aging. An initial epigenetic age reversal rate of several years per month has been noted with the SC protocols herein.

Administering SC nutrition will encourage senescent cell replacement in the presence of sufficient viable SCs, aided when MS1 is set to fission. Fission is required for senescent cell apoptosis and SC differentiation, where one SC divides into two daughter cells—one SC and the other somatic. Senolytic agents may be used when senescent cells have become resistant to apoptosis.

Stem cells have functional mitochondria, but these mitochondria are kept in a quiescent state by UCP2 channels that allow the passage of protons through the inner membrane without doing useful work, thereby substantially preventing the production of ATP. While not wishing to be bound by theory, it is believed that blocking UCP2 channels will provide the necessary stimulation for ATP production to begin proliferation, switching MS2 to the on state. Nanoparticles such as fullerenes can provide such blocking. Fullerenes are preferred due to their generally spherical shape and uniform size, while $C_{60}$ is most preferred as it is the most available, least expensive, has a known predilection for mitochondria, and is known to be nontoxic. The diameter of $C_{60}$ molecules at 0.7 nm is nearly a million times larger than the proton diameter, but protons in an aqueous environment form hydronium ions ($H_3O^+$), which then cluster with water molecules to form hydrated hydronium. Recent research suggests that the actual ion is $H_{13}O_6^+$. In any case, such water clusters ferrying protons have a significant size that is comparable to $C_{60}$ molecules. Thus when the conical topology at either distal end of UCP2 is blocked by a $C_{60}$ molecule, hydrated hydronium clusters cannot dock or discharge there and the leakage of protons is halted. Mitochondria thus begin generating ATP and quiescence is banished. With mitochondria in a fused state, stem cells are directed to symmetric proliferation and stem cell pools are enlarged.

If molecular size and physical blocking of UCP2 pores are the controlling factors as described, then fullerenes may have quite different chemical properties and still function to stimulate stem cells.

Referring now to the drawings wherein like numerals refer to like parts, FIG. 1 shows a cutaway section of a mitochondrion generally indicated by numeral 101 in an intermediate state between fusion and fission with bacterial-style loops of mtDNA 112, 113; cytosol 170, the jelly-like fluid in which the mitochondrion 101 is embedded; inner mitochondrial membrane 114; viscid matrix 116 in which oxidative processes occur; cristae 119, whereby the surface area of the inner membrane is increased; outer membrane 118; and intermembrane space 120 between inner membrane 114 and outer membrane 118.

If fissioned along axis 2-2, the mitochondrion 101 would be split into two generally spherical mitochondria with each portion containing one loop of mtDNA 112, 113, whereas in a fusion state the mitochondrion 101 would merge with other mitochondria along axis 1-1 and contain many loops of mtDNA. In a state of hyperfusion, it might contain hundreds. In the limit, all mitochondria in a cell might be interconnected in threadlike fashion. In that state, all enzymes would be shared.

Figure 2:
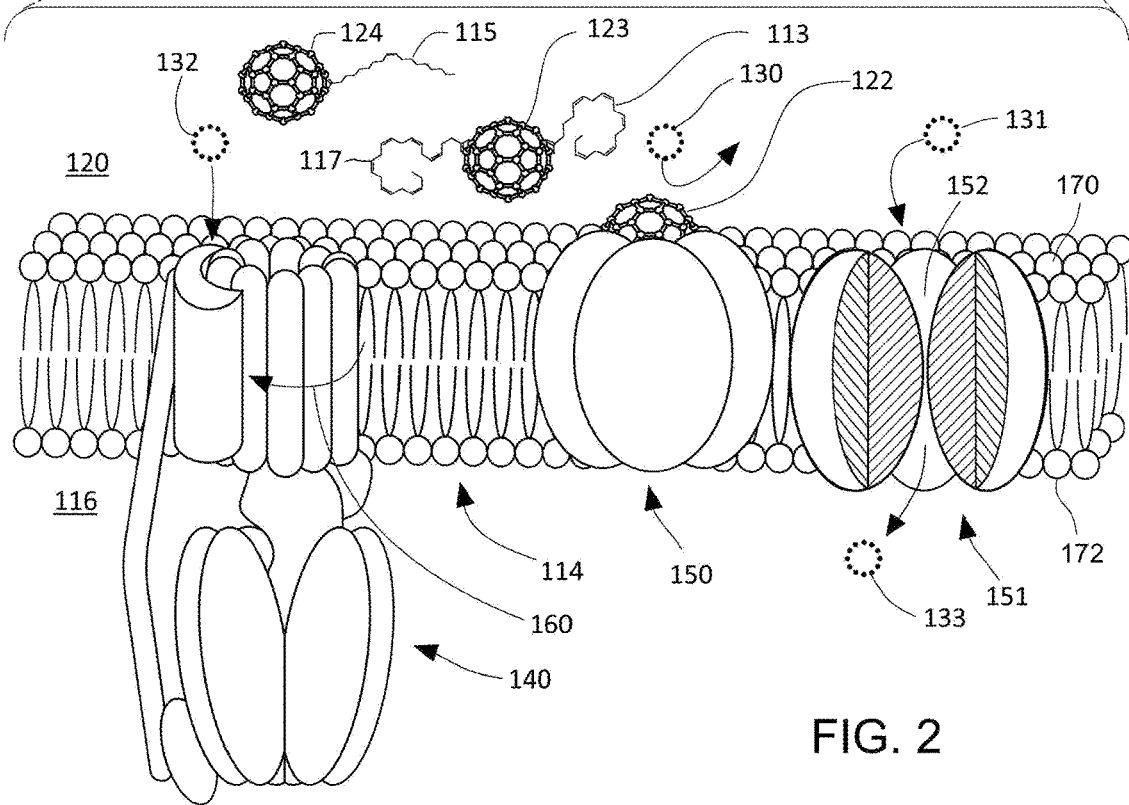
FIG. 2 is an idealized cross-sectional view showing the region around the mitochondrial inner membrane in more detail.

FIG. 2 shows an enlarged cross section of mitochondrial inner membrane 114, which is approximately 5 nm in wall thickness. Studded in the inner membrane 114 are enzymes ATP synthase 140, which are molecular turbines that channel the return flow of protons derived from hydrated hydronium 132 to convert ADP mechanically and catalytically to ATP. The lower part of ATP synthase 140 extends into the matrix 116, while the upper portion is buried in the inner membrane 114 and rotates in the direction 160. It has been measured to spin at 130 revolutions per second (7,800 rpm). The lower portion of ATP synthase 140 carries enzymes whereby ADP is converted to ATP.

The inner membrane 114 is also studded with various proteins and enzymes for oxidative processes and for pumping protons from the matrix 116 into the intermembrane space 120. These are well known in the art and are not shown here. In stem cells the inner membrane 114 is richly studded with UCP2 channels such as 150 and 151 (the latter shown in cutaway section) that allow protons to bypass ATP synthase 140 and return to the matrix 116 without creating ATP. According to the present hypothesis, molecules of $C_{60}$ 122 (sans adducts), 123 (with eicosapentaenoic acid (EPA) adduct 113 and docosahexaenoic acid (DHA) adduct 117), and 124 (with oleic acid adduct 115), can reversibly block UCP2 channels 150 and 151 to prevent return leakage of protons derived from hydrated hydronium 130, thus temporarily boosting ATP production. UCP2 channel 150 is shown blocked by $C_{60}$ molecule 122, repelling hydrated hydronium 130. While specific adducts are shown, they are not believed necessary for UCP2 blocking.

With UCP2 pores blocked, outer surface 170 of the inner membrane 114 will become positively charged relative to the inner surface 172 of inner membrane 114 as protons continue to be pumped from the matrix 116, however, whether protons approach UCP2 pore 150 along surface 170 or via hydronium ions 130, they will be physically blocked by $C_{60}$ 122. Additionally, fullerenes are conductive and thus $C_{60}$ 122 facing the intermembrane space 120 is expected to become positively charged and repel hydronium 130 even more efficiently. As yet unblocked UCP2 pore 151 allows hydrated hydronium 131 (or the proton derived therefrom) to pass down channel 152 where it reappears (or is reconstituted) as hydrated hydronium 133.

With UCP2 pores substantially blocked, MS2 is switched on, the matrix 116 pH rises, increasing the flow of protons through ATP synthase 140. In somatic cells with few UPC2 channels, this produces a relatively small boost in ATP output, but in stem cells with large numbers of UCP2 channels and thus quiescent mitochondria, this produces a far more dramatic boost, stimulating them into either proliferation or differentiation.

While the actual manner in which UCP2 pores allow proton leakage is not well understood, it is believed that $C_{60}$ shuts down this pathway, and whether that occurs by physically and/or electrostatically blocking UCP2 channels thereby preventing conduction of protons (or hydronium), or interfering with protons derived from hydronium transferred to a UCP2 channel, the end result is the same: stem cells are stimulated into an active state in the presence of $C_{60}$ by preventing return bypass of protons through UCP2 pores to the matrix, thereby increasing ATP output.

Fullerenes dissolved in oils can be delivered orally, and when employed with a SC protocol with a fused mitochondrial morphology, $C_{60}$ has been found efficient at reversing epigenetic age. Olive oil was preferred by Moussa et al., but many other oils may be used. Natural oils have hundreds of components, some yet unknown, and some capable of reacting with $C_{60}$. Thus processed oils are preferred for consistency. Highly refined MCT oils, for example, can dissolve $C_{60}$ while producing few if any adducts. MCT oils are medium chain triglycerides with aliphatic tails of 6-12 carbon atoms, and preferably comprising primarily caproic and/or caprylic acids. MCT oils are readily available and widely consumed. They have lower viscosity and thus more rapidly dissolve $C_{60}$, and are more stable than olive oils. Solution concentrations approaching 0.5 g/L are possible by grinding $C_{60}$ crystals to increase dissolution rate and magnetically stirring at room temperature for a period of approximately 2 weeks, or until substantially dissolved. The actual period is sensitive to the degree of grinding of $C_{60}$ crystals and their purity. The higher the purity the more perfect the crystals, and the more refractory to dissolution. The finished product may then be filtered, but this is considered generally unnecessary. Increasing the temperature during stirring will dramatically increase the dissolution rate of $C_{60}$. Free fatty acids may also be used, such as oleic acid. Dissolving $C_{60}$ in free fatty acids readily creates adducts (unlike with MCT or other purified oils), and heating substantially above room temperature results in rapid additions of adducts and rapid dissolution, with much higher concentrations. The resulting formation of adducts has not been found to interfere in stimulating stem cells, though the permeability of the blood brain barrier (BBB) may be sensitive to adduct type.

Example: A 5 mg/ml concentration of $C_{60}$ was prepared by stirring in oleic FFA at 75° C. for 3 hours, which is approximately five times the concentration achievable in olive oil and ten times that in MCT oil at room temperature. The whiskey color of the resulting mix resembled the color of $C_{60}$ often achieved in olive oil, suggestive of random oleic acid adducts in both, whereas $C_{60}$ dissolved by stirring in MCT oil at room temperature for two weeks produces the classic purple color of $C_{60}$ solutions in non-reactive solvents such as toluene, suggestive of no adducts. C60 in MCT oil produces results similar in character when taken at the same dosages of $C_{60}$ with a mitochondrial fusion promotor and stem cell nutrition, however $C_{60}$ dissolved in oleic FFA with heat provides effects subjectively stronger than $C_{60}$ dissolved in MCT oil for the same $C_{60}$ content. This may result from more efficient transport of $C_{60}$ with oleic acid adducts into mitochondria.

Mitochondrial fission and fusion can be achieved with commonly available supplements. Of the mitochondrial fusion promoters known in the art, stearic acid and sulforaphane are preferred. Those fusion promoters most preferred herein comprise stearic acid precursors such as triglycerides with at least one stearic acid moiety, stearic acid diglyceride and stearic acid monoglyceride (glycerol monostearate), and/or a sulforaphane source such as sulforaphane glucosinolate, generally with an activating enzyme such as myrosinase. These may be conveniently dosed orally, with minimum effective amounts of 500 mg or more for stearic acid as a monoglyceride, and 5-500 mg or more for sulforaphane, with a preferred range of 25-200 mg. Once mitochondrial morphology proceeds to complete fusion (though not necessarily hyperfusion), excess stearic acid only serves to produce longer periods of fusion as it is cleared from the body. While stearic acid has a half-life of ten to twelve hours, the fusion state is needed only until stem cells commit to symmetric proliferation. Sulforaphane has a half-life of about an hour and peaks in the bloodstream in as little as 15 minutes, and thus may be used simultaneously with $C_{60}$. Another fusion promoter that acts rapidly is glycerol monostearate, which may be used simultaneously with a UCP2 pore blocker. Given its much greater speed, the dose required is much less, as is the residual fusion effect. Any substantially nontoxic and digestible source of stearate may be used, though they may have decreasing levels of bioavailability, thus requiring longer digestion times and/or larger doses. These comprise triglycerides with one to three fatty acid moieties with at least one moiety being stearic acid. Commercial sources of stearic acid are generally impure. Food grade stearic acids, for instance, can comprise more palmitic acid than stearic acid. Nevertheless, they have proven effective in the SC protocols in the amounts stated herein, based on the free fatty acid (FFA) content. Triglycerides are rendered more bioavailable by dispersing in hot foods, or in such products as cookies and brownies. (Since they melt during baking, they can replace vegetable oil.) Metal stearate soaps appear to be less bioavailable. Sodium and potassium stearates can be dissolved in hot water, and thus could be used when dispersed in like manner to food grade stearic acid triglycerides. Other fusion promoters (and fission inhibitors) are known and have been used to reduce ischemia/reperfusion injury and could be used here. One example is mitochondrial fusion promoter M1 (1-(5-Chloro-2-hydroxyphenyl)-ethanone 2-(2,4,6-trichlorophenyl)hydrazone).

The fullerene $C_{60}$ dissolved in triglycerides is presently sold as a health supplement, however such supplements do not contain sufficient stearic acid to create a state of mitochondrial fusion, and in any case the fusion would come too late, after stem cells have committed to asymmetric replication. $C_{60}$ dissolved in triglycerides or FFAs has been found to act rapidly, producing an energy boost in thirty minutes or less when taken on an empty stomach, while triglycerides take more than an hour to digest and absorb, thus stearic acid triglycerides are preferably administered more than an hour before $C_{60}$, more preferably two hours, and most preferably three hours. Glyceryl monostearate (GMS) may be used simultaneously as a unitary dose as it is rapidly absorbed.

Another alternative for a unitary dose is to delay the absorption of the fullerene portion by providing a matrix or coating to slow dissolution. An enteric coating is one example, but many methods of controlling and delaying drug delivery are well known in the art and may be used here. While this delay may be helpful, the absorption of fullerenes combined with oil are already delayed over water soluble substances, which is generally sufficient when used with GMS.

For asymmetric SC division (differentiation), or to enhance apoptosis of senescent cells, mitochondria are stimulated with a mitochondrial fission (fragmentation) promoter. This sets mitochondrial switch 1 (MS1) to fission. For most cell types, this can be achieved by administering a $NAD^+$ promoter. Such promoters comprise nicotinic acid, nicotinamide, nicotinamide riboside (NR), nicotinamide and ribose (NAM+R), nicotinic acid and ribose, nicotinamide mononucleotide, and oxidized nicotinamide adenine dinucleotide. NAM+R is preferred for low cost, easy availability, and low toxicity. NAM+R may be conveniently dosed orally, with minimum effective amounts ranging upward from 100 mg each for nicotinamide and ribose, and preferably half a gram of each, and more preferably one gram of each. Five grams or more of each may be used, but is unnecessary. After mitochondrial fission proceeds to completion, excess promoters only serve to maintain fission until $NAD^+$ is reduced to NADH, thus lowering the $NAD^+$/NADH ratio, or fission is otherwise overridden by supplementation with a fusion promoter such as stearic acid.

While a high $NAD^+$/NADH ratio promotes fission, stearic acid in the doses discussed has been found to promote fusion more profoundly, thus the latter overrides the former: e.g., 10 grams of food grade triglyceride comprising approximately 50% stearic acid moieties will override 2 grams each of nicotinamide and ribose taken some hours before, while one gram of GMS will override it for a short time.

SENESCENT CELLS AND TELOMERES

Although stem cells produce telomerase, it is known that this enzyme can nevertheless fail to maintain telomere length. Some may therefore find it desirable to extend telomeres during proliferation from time to time. Telomerase stimulating supplements comprise cycloastragenol and astragalus extracts that are known to contain cycloastragenol and other putative telomerase agonists. In the present invention, it is generally not desirable that telomeres of somatic cells be extended, as this would allow epigenetic age to increase by suppressing senescence and apoptosis. Thus telomerase stimulating supplements should be used rarely, or not at all.

Senolytic treatments reduce the population of senescent cells more rapidly than natural processes. While senescent cells aren't rendered senescent because of their advanced epigenetic age, they are generally among the epigenetically oldest cells of the body. And while they are cleared naturally, this process can lag with age and with the declining availability of functional stem cells to replace them. Non-limiting examples of senolytic substances include dasatinib, quercetin, navitoclax, piperlongumine, butyrate, fisetin, curcumin and curcumin analogues. Many others are known.

It is suggested herein that clearance of senescent somatic cells naturally declines when new somatic cells derived from stem cells are not available to replace them, and increases when stem cell pools are filled and healthy, both due to paracrine signaling. Thus enhancing stem cell pools should enhance senolytic treatments, as should administering stem cell nutrition during senolytic treatment.

It has been estimated that some 50 billion senescent cells are recycled daily by apoptosis. Apoptosis is an orderly form of cellular suicide that is much less toxic to the body than necrosis, though effects can still be perceived. An effective senolytic treatment would necessarily increase the average rate substantially before subjective effects could be easily distinguished over baseline. These effects are often described as flu-like symptoms such as muscle pains and lethargy. In fact, the influenza virus is known to stimulate cellular apoptosis, which is necessary for spreading viral particles. The symptoms produced by senolytic treatments may be reversed with stearic acid, showing that mitochondrial fusion ends apoptosis, thus fusion blockers such as stearic acid and/or sulforaphane should prove useful in interrupting viral pathogenesis, slowing or stopping the exponential growth of virions as immunity is built up. Other widespread viruses that spread by apoptosis and thus might be slowed or stopped by fusion promoters are herpes simplex, HIV, and SARS-CoV-2. The Ebola virus stimulates massive apoptosis, thus fusion promoters might be particularly helpful.

It is known in the art that apoptosis begins with mitochondrial fission, which can be achieved with $NAD^+$ precursors such as NAM, NAM+R and/or apigenin (4',5,7-trihydroxyflavone), as nonlimiting examples. A series of cellular enzymes (caspases) then act in a cascade, driving senescent cells into programed apoptosis.

Of particular use for removing senescent cells are nicotinamide and ribose (NAM+R) to stimulate fission, along with curcumin (preferably liposomal, phytosomal, or with other enhancement to improve bioavailability) and/or resveratrol to promote caspase activation. Curcumin and resveratrol appear to work synergistically with mitochondrial fission in removing senescent cells by apoptosis.

ENHANCING STEM CELL POOL EXPANSION

Cell signaling modulators can increase the numbers of SCs generated and increase their utilization. Many signaling pathways of the autocrine, paracrine and endocrine types are known. Examples of paracrine signaling pathways useful in the present invention are the Hedgehog, Wnt, FGF, and TGF-β pathways.

Three Hedgehog homologues are known: Sonic (Shh), Desert (DHH), and Indian (IHH). Shh is a morphogen and mitogen that stimulates NSC proliferation. Smoothened agonist (SAG) is an exemplary Shh agonist for NSC proliferation, as is the amino acid taurine and the dietary supplement resveratrol. In animal studies, SAG has been used at 10 mg/kg, but it is expected far less would be required for this protocol. For a human subject, taurine at 5 mg/kg to 1 g/kg is considered a useful therapeutic range, with 20-200 mg/kg preferred, and 30-60 mg/kg most preferred. For resveratrol, doses of 0.5-20 mg/kg are considered a useful therapeutic range, with 1-10 mg/kg preferred, and 2-5 mg/kg most preferred.

Figure 3:
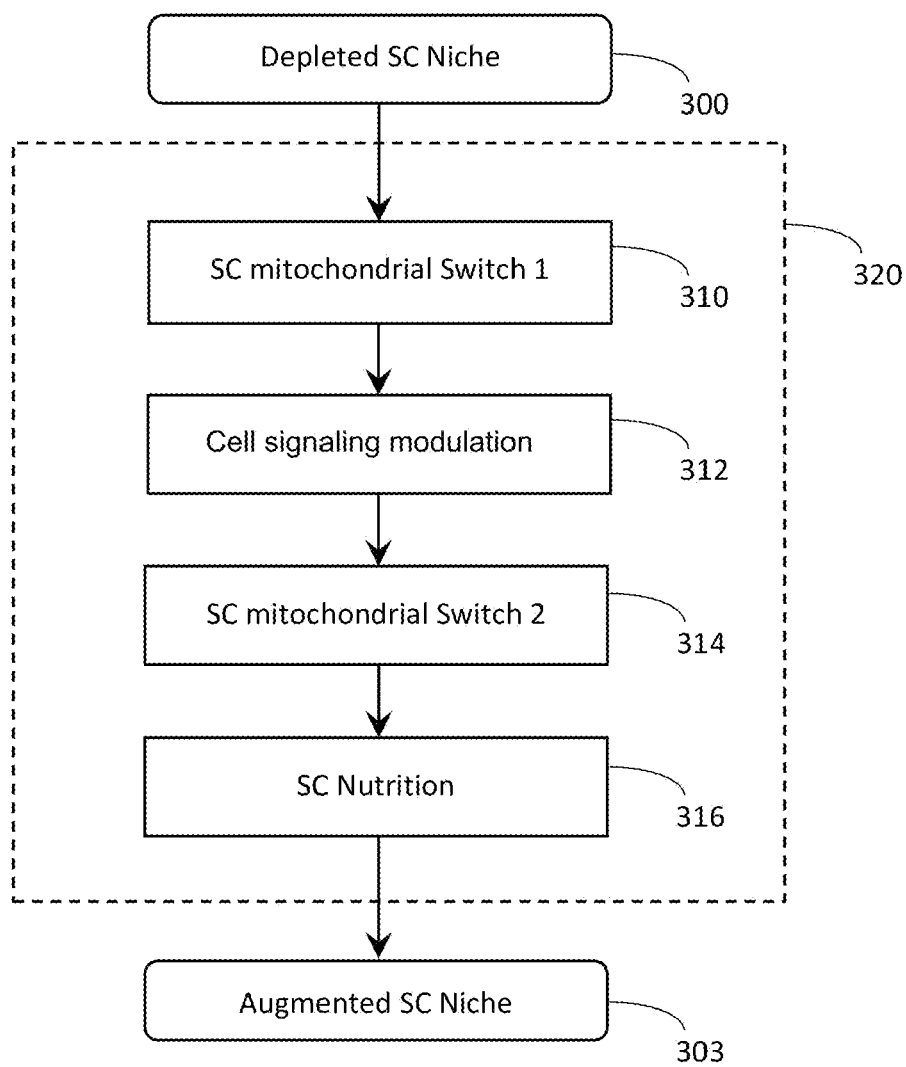
FIG. 3 is a flowchart of the inventive method showing the sequence of mitochondrial switches and cell signaling for filling stem cell pools.

Turning again to the drawings, FIG. 3 shows a flowchart of the inventive method in which a subject has a depleted SC pool 300 before SC replenishment, indicated by dashed box 320. SC replenishment step 320 comprises steps 310, 312, 314, and 316. At step 310 (MS1), SC mitochondria are driven into fusion. At step 312, cell signaling is modulated. This may occur before, during, or after step 310. Resveratrol and taurine are examples of modulators that may be used to modulate Shh signaling. Sirt3 promoters may also be employed as modulators. Examples are pyrroloquinoline quinone (PQQ), methylene blue (MB), alpha lipoic acid (ALA), and Tauroursodeoxycholic acid (TUDCA). An example of autocrine modulation is the decrease of myostatin by creatine.

At step 314, SC mitochondrial ATP output is promoted (MS2), thereby beginning proliferation. As one example, C60 may be used to block SC mitochondrial UCP2 pores, switching MS2 on. SC nutrition is provided at step 316 to prevent cell arrest of newly created SCs. Nutrition may be provided before, during, or after step 314, and may be repeated at intervals after step 320. These intervals may vary from an hour to 24 hours, and nutrition can also be administered over subsequent days. The need may vary considerably depending upon the size of the stem cell pools and the demand for senescent cell replacement. The result of one cycle of SC replenishment 320 is an augmented SC pool 303. More than one cycle of step 320 is generally desirable. Once a week to once a month is a preferred schedule for maintenance.

Used herein, an SC pool generally refers to the population of SCs in the microenvironments known as SC niches, and also to the population of SCs in general circulation, such as mesenchymal stem cells (MSCs) and VSELs.

After sufficient SC treatment cycles have been achieved, SC niches may be full, or even over filled. It is expected that homeostatic mechanisms will trim excess SC pools either by terminal differentiation or by apoptosis. It is thus economical to administer nutrition to insure the excess is used for replacement and not wasted. Epigenetic age may continue to decline for days or weeks as stem cells with low epigenetic age replenish rapidly dividing transit cells (TACs), which in many organs do the bulk of the replicative work providing the organism with new somatic cells. These TACs are expected to be most impacted by telomerase promoters, and thus such promoters should be used rarely or not at all, as they can rapidly increase average epigenetic age.

Figure 4:
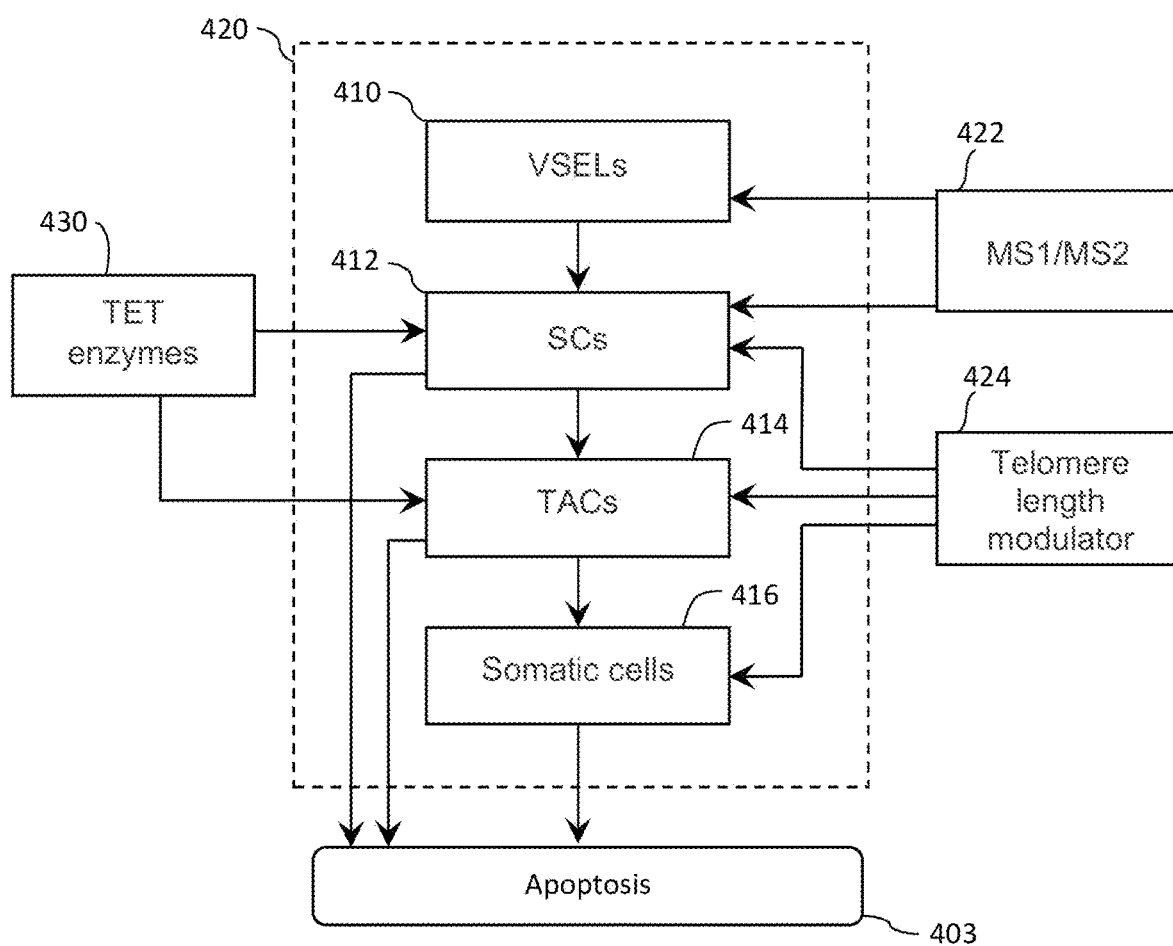
FIG. 4 is a flowchart of cell replacement showing points where replacement rate and methylation can be modified.

FIG. 4 is a flowchart of cell replacement showing points where SC replacement and chromosome methylation can be modified. Cell replenishment, indicated for a tissue by dashed box 420, is hierarchical. Circulating VSELs 410 can be employed to replace SCs 412 resident in a niche, which then replace senescent TACs 414 as needed, and which finally replace somatic cells 416 as they become senescent and are removed by apoptosis 403, or shed from the body as occurs with epidermal cells and enterocytes of the epithelium. Intervention with MS1 set to fusion and MS2 set to on at 422 will expand VSELs 410 and SCs 412, thereby increasing the rate of replacement of senescent TACs 414 due to higher availability. This will reduce the average epigenetic age of somatic cells 416. In contrast, intervention with a telomerase agonist 424 will slow the replacement of SCs 412, TACs 414, and somatic cells 416 by lengthening their respective telomeres and slowing or preventing senescence. Somatic cells 416 will thus become epigenetically older before apoptosis 403. Filling of SC niches lowers epigenetic age while lengthening telomeres increases it, thus the use of telomerase agonists should be minimized, or not used at all. Intervention with TET enzyme promoters 430 will remove aberrant methylation of SCs 412 and TACs 414 during SC proliferation, thereby further lowering epigenetic age of the organism.

Figure 5:
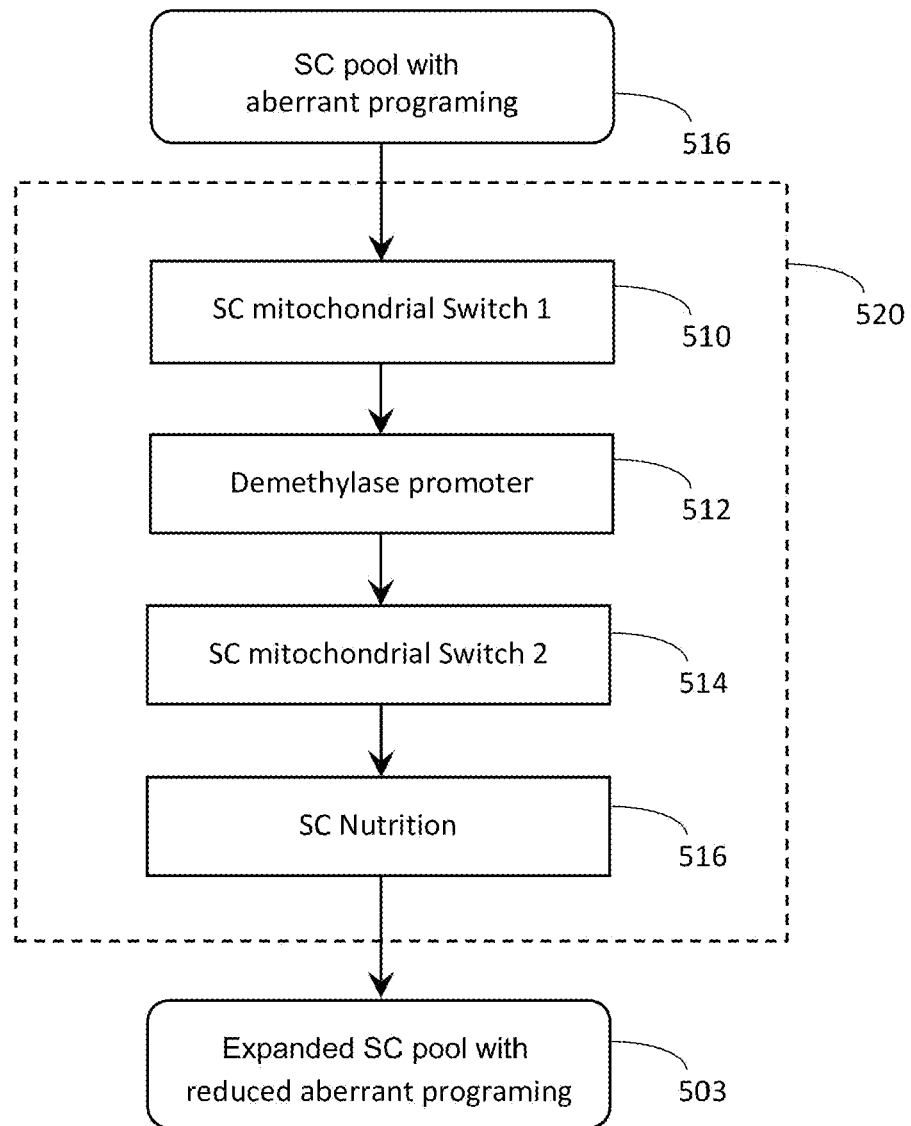
FIG. 5 is a flowchart of SC cell replacement showing points where aberrant methylation can be reduced.

FIG. 5 is a flowchart of SC cell replacement showing points where aberrant methylation can be reduced. An SC pool with aberrant programming is indicated by box 516, before SC replenishment and cleanup, indicated by dashed box 520. SC replenishment and cleanup step 520 comprises steps 510, 512, 514, and 516. At step 510 (mitochondrial switch 1), SC mitochondria are driven into fusion. At step 512, endogenous demethylase is stimulated with a promoter. This may occur before, during, or after step 510, and may comprise alpha-ketoglutarate (AKG) or a pharmaceutically acceptable derivative as previously noted. At step 514, MS2 is set to fusion and SCs proliferate with reduced aberrant methylation. SC nutrition step 516 comprises at least methionine and lysine. Step 520 may comprise a unitary dose of all administered components, which may also include cell signaling modulators.

The following example protocols been employed, with example doses that may be varied in the ranges listed in the Preferred Doses section. All amounts are for a male subject of about 80 kg:

TREATMENT RESULTS

Stem Cell Trial Results

A male subject, 66 years old and in substantially good health, trialed the stem cell protocol. After 3 months (34 SC replenishment treatments and one senolytic treatment) he found that pain in both knees and joint instability in one knee that had troubled him for years faded and disappeared, as did a needle-like pain in one patella when kneeling. He noted tighter and smoother skin and disappearance of all age wrinkles and most broken capillaries on his face. A skin pinch test (time to recovery after pulling up neck skin with two fingers) went from 3 seconds to 1. He noted greater muscle mass, less fat, and more stamina. His formerly flat feet developed a noticeable arch. Tenosynovitis in one palm disappeared. A distortion he had seen in the Amsler grid that had remained stable for approximately 15 years also disappeared.

These seemingly unrelated changes are consistent with systemic stem cell activity.

This subject had previously used $C_{60}$ outside of the protocol and found that initially positive results faded after a year and subsequent use of $C_{60}$ produced no effects at all apart from increased alcohol tolerance and exercise enhancement for a few hours, consistent with its antioxidant properties and the increase of ATP production in myocytes. It is believed that this fading was due to depletion of stem cell pools, which were then refilled using the protocols of the present invention.

Test subject's epigenetic age results are summarized below in the table of AR (Age Regression) trials:

TABLE 1

| AR Trial | Epigenetic - chronological age | Treatment (weeks) | Elapsed time (weeks) | Comments | Cocktails |
|---|---|---|---|---|---|
| 0 | +0.5 years | 0 | 0 | Baseline | — |
| 1 | −11.2 years | 12 | 20 | Mito switches | SSC1 |
| 2 | −13.0 years | 10 | 95 | Mito switches | SSC2 |

TABLE 1-continued

| AR Trial | Epigenetic - chronological age | Treatment (weeks) | Elapsed time (weeks) | Comments | Cocktails |
|---|---|---|---|---|---|
| 3 | −14.6 years | 8 | 105 | Mito switches/ resveratrol | SSC3 |
| 4 | −22.6 years | 8 | 143 | Mito switches/ AAKG | SSC3 |

The second column of Table 1 reports the difference between epigenetic and chronological age; the third column reports the weeks of treatment, wherein there was at least one fusion cycle per week and generally two fission cycles initially, decreasing to the end of this period to one treatment every week or two; the fourth column reports the total elapsed time from baseline; the fifth column reports the protocols used; and the sixth column reports the nutritional cocktails.

Several companies are presently offering epigenetic tests that purport to give epigenetic age that generally closely correlates with chronological age. The subject had taken a test offered by Osiris Green two months prior beginning treatment. This company found that epigenetic age can be reliably measured by sampling the methylation patterns of just three gene markers taken from buccal cells (similar to Weidner's clock, which uses 3 markers from blood), with an overall median absolute deviation of 1.8 years. The reported age after the subject's baseline trial (Trial 1) fell well within that range, with a calculated epigenetic age 0.5 years higher than his chronological age. This was in spite of his prior use of C60 for several years outside of the protocol.

A second epigenetic test after the first trial and 5 months after the baseline trial reported an estimated age more than 11.2 years below his first estimated age. This was far outside the expected range. A third test after the second trial showed a decline to 13.0 years below current age. A Sirt3 modulator (300 mg of resveratrol) was then added one hour before C60, and one treatment per week was performed for 8 weeks, resulting in an epigenetic age 14.6 years below his chronological age. The addition of 5 grams of AAKG to the mito switch protocol for 8 treatments over 8 weeks produced an overall decline from his chronological age of 22.6 years. It appears that using a demethylase promoter during stem cell stimulation produces a far more rapid decline in epigenetic age, as removing aberrant methylation is easiest during cell division. Removing aberrant methylation from the rapidly dividing TACs will produce results that will slowly fade, but removing methylation from SCs will produce the most long lasting results.

The epigenetic testing labs used—Osirus Green, TrueMe, EpiAging and Epimorphy—all used different sets of genes, yet results were within a few years for samples taken at the same time.

A separate trial using a telomere agonist (cycloasragenol) with mito switches was found to rapidly increase epigenetic age. It was initially hypothesized that any negative impact would be minimal if used only with mito switches, but the telomeres of rapidly dividing TACs were likely also lengthened, and this blocked TAC senescence and replacement. Since TACs divide frequently, they also experience rapid epigenetic aging, thus somatic cells derived from TACs with telomeres extended by an agonist reach higher epigenetic age that would ordinarily be possible.

STEM CELL NUTRITION

Some adult stem cells are known to require a specific group of nutrients, but it is likely that the nutritional requirements of all SCs are not yet known. The amino acid requirements of human embryonic cells (hESCs) in vitro include methionine and lysine, in particular, and also leucine. Absent some or all these amino acids, SCs may undergo cell arrest and ultimately progress to apoptosis. Thus they are included for SC nutrition. To these can be added the metabolic products S-adenosylmethionine (SAMe) derived from methionine, and β-hydroxy-β-methylbutyrate (HMB), derived from leucine. By avoiding cell cycle arrest when suitable nutrients are administered, fewer cycles of endogenous stem cell treatments are needed. The uptake of various amino acids vary widely according to conditions, thus for general purposes, methionine and lysine are supplemented, optionally with leucine, and optionally with a commercially available mix of essential amino acids. Supplementing SAMe in conjunction with fusion-biased self-renewal will further insure that self-renewal is achieved. Effective doses of SAMe in an adult human subject ranges from about 1 mg to about 1 g, with a preferred range of about 5 mg to about 100 mg. The proliferation of NSCs is enhanced by the amino acid taurine. Thus taurine may be used as a nutritive addition, in particular when NSC pools are to be enhanced. This may be used in conjunction with the stem cell modulator and antioxidant TUDCA, and a fusion supplement such as sulforaphane or a $NAD^+$ enhancer. Effective doses of taurine in an adult human subject range from about 500 mg to about 50 g, with a preferred range of about 2 g to about 20 g.

Herein it is expected that the requirements of different stem cell types will vary, along with individual differences from one subject to the next, as will the nutrients already available endogenously. Thus there is likely no one best nutritional cocktail. In fact, use of amino acids that stimulate stem cells may be decidedly unhealthy in the long run when used outside the present SC protocol. As discussed above, methionine depletion can result in pluripotent SC arrest and apoptosis. And when methionine is readily available, it is expected that pluripotent stem cell activity will increase. But without sufficient proliferation, pluripotent SCs can become depleted over years of use. With the appropriate use of mitochondrial switches to expand reserves of pluripotent SCs, however, it becomes unnecessary to starve oneself to live longer.

EXAMPLES OF SC NUTRITIONAL SUPPLEMENT COCKTAILS

The following examples of antiaging cocktails of amino acids have been employed. All amounts are for a male subject of about 80 kg:
Example SCC1 (316)
Threonine, 3 g
Methionine, 2 g
Lysine, 2 g
Leucine, 2 g
Example SCC2 (316)
SC nutritional cocktail
Threonine, 3 g
Methionine, 2 g
Lysine, 2 g
Leucine, 2 g
Tryptophan, 500 mg
SAMe, 100 mg
Example SCC3 (316)
SC nutritional cocktail
Methionine, 2 g
Lysine, 2 g
Example SCC4 (316)
SC nutritional cocktail
Methionine, 2 g
Lysine, 2 g
Taurine, 5 g In the above nutritional examples, amino acids can be administered in capsules or tablets, or by dissolving or dispersing in fruit juice or flavored water. A mix comprising at least 5% each of methionine and lysine is preferred, and at least 10% most preferred.

EXAMPLE PROTOCOLS FOR EPIGENETIC AGE REGRESSION

Example P1
SC replenishment, as a single dose:
GMS, 1 g
$C_{60}$, 3 mg in oil
Example P2
SC replenishment, as a single dose:
GMS, 1 g
DHM, 500 mg
$C_{60}$, 3 mg in oil
Example P3
SC replenishment, as a single dose:
GMS, 1 g
$C_{60}$, 3 mg in oil
Supplements of cocktail examples SCC1-4
Example P4
SC replenishment:
Stearic acid triglyceride, 10 g, dispersed for oral availability
After 3 hours
$C_{60}$, 3 mg in oil
Supplements of cocktail SCC1-4
Example P5
SC replenishment combined with mitochondrial cleanup, as a single dose:
$C_{60}$, 3 mg in oil
Supplements of example Mito1-2
Supplements of cocktail examples SCC1-4
Example P6
Senescent cell replacement with mitochondrial cleanup, as a single dose:
Curcumin, 2 g, liposomal
Supplements of example Mito1
Supplements of cocktail example SCC1-3
In all examples herein, a human subject of 80 kg is assumed.

MITOCHONDRIAL AGE REVERSAL

The mtDNA of mitochondria age in parallel fashion to nDNA, with mutations of the mtDNA genome and additions of epigenetic marks that degrade performance. In the case of mtDNA, the marks are methyl groups that reduce ATP output. Most genes coding for mitochondria are located in the nDNA, but the 37 genes of human mtDNA code for 13 polypeptides necessary for the Krebs cycle. If just one mutated gene fails to function, then the full Krebs cycle cannot be supported by that mtDNA loop when isolated in a fissioned mitochondria. The membrane potential ($\Delta\Psi m$) falls to zero, allowing such mitochondria to be labeled by the PINK1/Parkin quality control process that ultimately results in degradation in lysosomes. The efficiency of this process declines in aged cells and defective mitochondria appear that are resistant to natural fission and thus resistant to mitophagy. Methylation of mtDNA also increases with age. Mitochondria with single loops of hypermethylated mtDNA that have lower but nonzero $\Delta\Psi m$ are protected from mitophagy. It is herein hypothesized that lower ATP (and ROS) activity partially protects methylated mtDNA from mutations, providing a survival advantage over unmethylated mtDNA. With lower rates of mutation, hypermethylated mtDNA may ultimately come to dominate cellular populations.

In the present invention, fission is alternated with fusion to greatly magnify the endogenous quality control process. This alone is not sufficient for a full restoration of function, however, as the membrane potential does not go to zero for isolated methylated mtDNA that are otherwise unmutated, and thus are retained and duplicated during mitogenesis. It is suggested herein that numerous maladies of aging are at least partially due to the buildup of methylated and hypermethylated mtDNA. These include frailty, hypertension, fatigue, immune system decline, and many other characteristics of aging that can be symptoms of ATP deficiency. Thus reducing the methylation of mtDNA in the elderly and others with a deficiency should ameliorate these symptoms. As there appears no natural quality control program analogous to PINK1/Parkin to effectively remove mtDNA methylation, a similar cyclic method previously used for removing aberrant methylation from nDNA was trialed. Fission and fusion cocktails Mito1 and Mito2 were alternated on a substantially daily basis. Mito1 comprised a unitary dose of a fission promoter (NAM), a biogenesis promoter (PQQ), and a demethylase promoter (AKG), while Mito2 comprised a unitary dose of a fusion promoter (GM), a biogenesis promoter (PQQ), and a demethylase promoter (AKG).

It was hypothesized that using biogenesis during fission to reduce membrane potential to zero would preferentially expose methylated mtDNA to the PINK1/Parkin QC process, marking these mitochondria for mitophagy. Isolated mtDNA loops with the greatest methylation would have the least reserves of enzymes during biogenesis and thus would be the most likely to be labeled for removal. Methylation would also be lost by the action of demethylase enzymes during biogenesis, a point where methyltransferase enzymes cannot restore them.

Preferred biogenesis promoters include pyrroloquinoline quinone (PQQ), its esters, isomers, and derivatives thereof. Methylene blue and its analogues also stimulate biogenesis and cross the BBB, and are thus preferred for treating neuronal mitochondria.

A preferred demethylase promoter is alpha-ketoglutarate (AKG). Pharmaceutically acceptable derivatives of alpha-ketoglutarate may be chosen from the nonlimiting group consisting of ammonium alpha-ketoglutarate, arginine alpha-ketoglutarate, calcium alpha-ketoglutarate, creatine alpha-ketoglutarate, glutamine alpha-ketoglutarate, leucine alpha-ketoglutarate, lithium alpha-ketoglutarate, magnesium alpha-ketoglutarate, potassium alpha-ketoglutarate, sodium alpha-ketoglutarate, taurine alpha-ketoglutarate, and the like. Alpha-ketoglutarate is preferred due to its speed of action.

A preferred fusion promoter is GMS for its speed of action. Other stearic acid sources may be used if the biogenesis promoter is delayed release or taken at a later time. A nonlimiting group of stearic acid sources include food grade "stearic acid," which is a triglyceride of stearic and palmitic acids, and natural butters (also called oils) that have substantial stearic acid content, such as mango kernel, kokum, shea, cocoa, sal, and illipe. Others may be chosen from the group comprising FFAs and monoglycerides comprising stearic acid in the combined dose of about 50 mg to about 20 g stearic acid, diglycerides comprising stearic acid in the range of about 100 mg to about 20 g, triglycerides comprising stearic acid in the range of about 2 g to about 40 g, and sodium and potassium stearates comprising stearic acid in the range of about 2 g to 40 g. Still others comprise sulforaphane or sulforaphane precursors in the range of about 5 mg to about 5 g.

A preferred fission promoter is NAM+R. Alternatives comprise one or more of the group that includes nicotinamide, nicotinic acid, nicotinamide riboside, nicotinamide mononucleotide, oxidized nicotinamide adenine dinucleotide, and apigenin, with a combined dose of about 80 mg to about 8 g. Ribose may be added in amounts preferably between 80 mg to about 20 g.

In a trial, Mito1 and Mito2 were administered on alternate days as unitary doses, with impressive results as shown below in Table 2, and in FIG. 7. Examples of supplement cocktails are listed below as Mito1 to Mito3.

Figure 6:
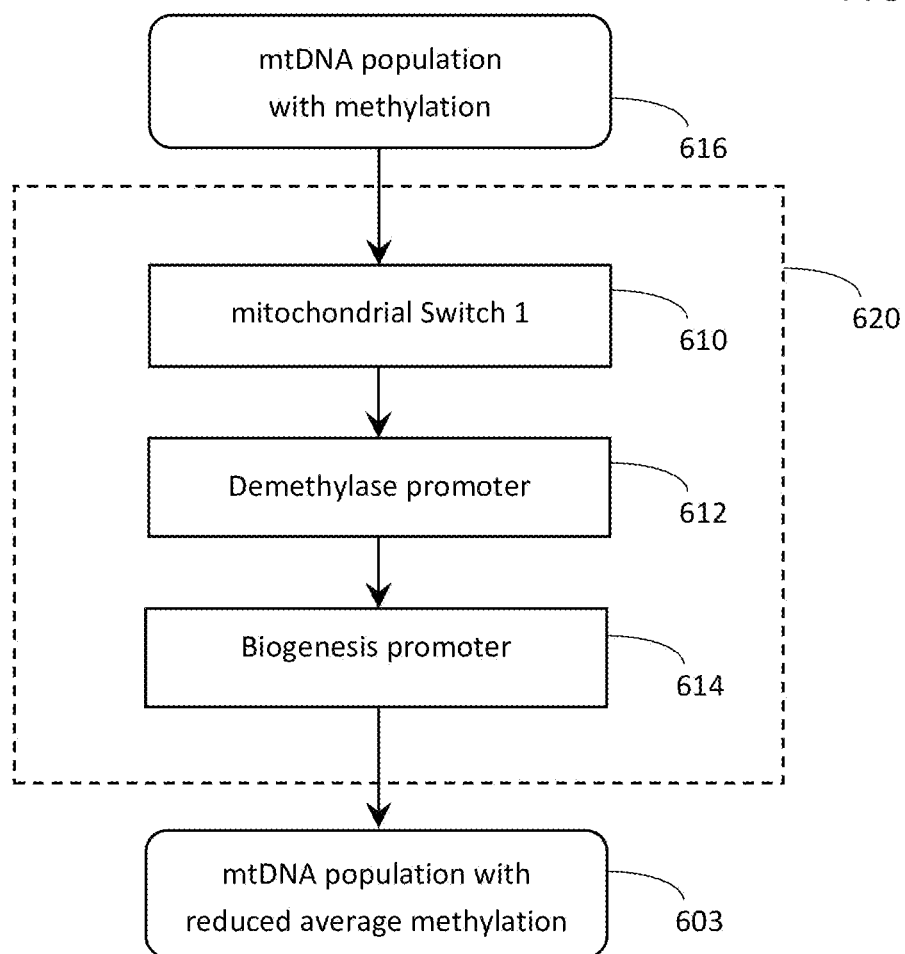
FIG. 6 is a flowchart of mitochondrial treatment showing the sequence of steps producing a lower average mitochondrial methylation.

Turning again to the drawings, FIG. 6 is a flowchart of mitochondrial mtDNA cleanup showing the sequence of steps producing a lower average genetic and epigenetic (methylation) damage. A cellular population of mtDNA having an average methylation 616 is cleaned up in the combined step designated by dashed box 620. Cleanup 620 comprises sub-steps 610, 612, and 614. At sub-step 610, mitochondrial switch 1 (MS1) is set to fusion. At sub-step 612, endogenous demethylase is stimulated. This may occur before, during, or after sub-step 610, and may comprise alpha-ketoglutarate or a pharmaceutically acceptable derivative from the nonlimiting group previously noted. At sub-step 614, biogenesis is stimulated. This will temporarily increase the mitochondrial mass, while homeostatic mechanisms will then lower it again by mitophagy. Mitochondrial mass and average methylation can be lowered more quickly by repeating step 620 with MS1 in sub-step 610 set to fission. To achieve the most rapid removal of mitochondrial damage, step 620 is repeated while necessarily varying only MS1 of sub-step 610 between fusion and fission. By using rapidly absorbed promoters, step 620 can comprise a single, unitary dose. The period between fission and fusion doses is preferably at least 8 hours, more preferably at least 12 hours, and most preferably at least 24 hours.

Cycling the procedure in FIG. 6 with MS1 switched between fusion and fission will quickly restore ATP output, using the unitary doses Mito1 and Mito2 described in the exemplary supplement cocktails listed below. The process can begin with either Mito1 or Mito2, while Mito3 can be used as a maintenance dose, or used alone.

Example Mito1 (fission)
mtDNA cleanup cocktail:
NAM+R, 1 g of each
AKG, 1 g
PQQ, 20 mg
Example Mito2 (fusion)
mtDNA cleanup cocktail:
GMS, 1 g
AKG, 1 g
PQQ, 20 mg
Example Mito3
mtDNA maintenance:
AKG, 1 g
PQQ, 20 mg In the above nutritional examples, cleanup cocktails can be administered in capsules, caplets or tablets, as a paste or powder, by dissolving or dispersing in fruit juice or flavored water, or by any other method found satisfactory by the subject.

MITOCHONDRIAL TRIAL RESULTS

This trial examined the effects of using a cyclic protocol for removing methylation marks from mtDNA. Example cocktails Mito1 and Mito2 were alternated on a substantially day-to-day basis, as shown in Table 2.

TABLE 2

| Day | Reps | Δ | Δ % | Protocol |
|---|---|---|---|---|
| 1-3 | 16 | — | — | Baseline |
| 4 | 12 | — | — | Mito1 |
| 5 | 21 | 9 | 42.9 | Mito2 |
| 6 | 13 | — | — | Mito1 |
| 7 | 21 | 8 | 38.1 | Mito2 |
| 8 | 22 | — | — | — |
| 9 | 23 | — | — | Mito2 |
| 10 | 18 | — | — | Mito1 |
| 11 | 23 | 5 | 21.7 | Mito2 |
| 12 | 17 | — | — | Mito1 |
| 13 | 22 | 5 | 22.7 | Mito2 |
| 14 | 19 | — | — | Mito1 |
| 15 | 22 | 3 | 13.6 | Mito2 |
| 16 | 22 | — | — | Mito1 |
| 17 | 22 | 0 | 0.0 | Mito2 |
| 18-33 | 22 | 0 | — | — |

The 69 year-old subject counted the number of reps to exhaustion for twenty-pound dumbbell curls in his non-dominant hand, approximately five hours after taking the oral composition of either protocol composition Mito1 (fission) or Mito2 (fusion). Clearly, Mito2 initially increased reps over baseline while Mito1 decreased them. The difference between the reps of Mito2 and the previous day's Mito1 are shown under the heading Δ, while the Δ% column shows Δ divided by that day's Mito2 result as a percentage. It is expected that this percentage reflects the magnitude of damage to mitochondria. Damage is primarily a combination of mutations that affect one or more mtDNA genes, sending $\Delta\Psi m$ to zero during fission, and mtDNA methylation that reduces $\Delta\Psi m$ during fission, but not to zero. If all mitochondria were genetically damaged, it was expected Δ% would be 100%. If there were no damage, either genetic or epigenetic, it was expected Δ% would be 0%, while with only methylation damage, Δ% would be intermediate.

Damage due to mutations can be cleared by natural quality control via PINK1/Parkin by alternating fission with fusion, but the reduction of $\Delta\Psi m$ due to methylation cannot be cured in this way. It was hypothesized that by promoting biogenesis during fission, low $\Delta\Psi m$ of mtDNA loops could be further reduced to zero and the loops removed by PINK1/Parkin. And even if some loops were not removed, their methylation level would be reduced by TET enzymes, thus lowering Δ% incrementally.

Figure 7:
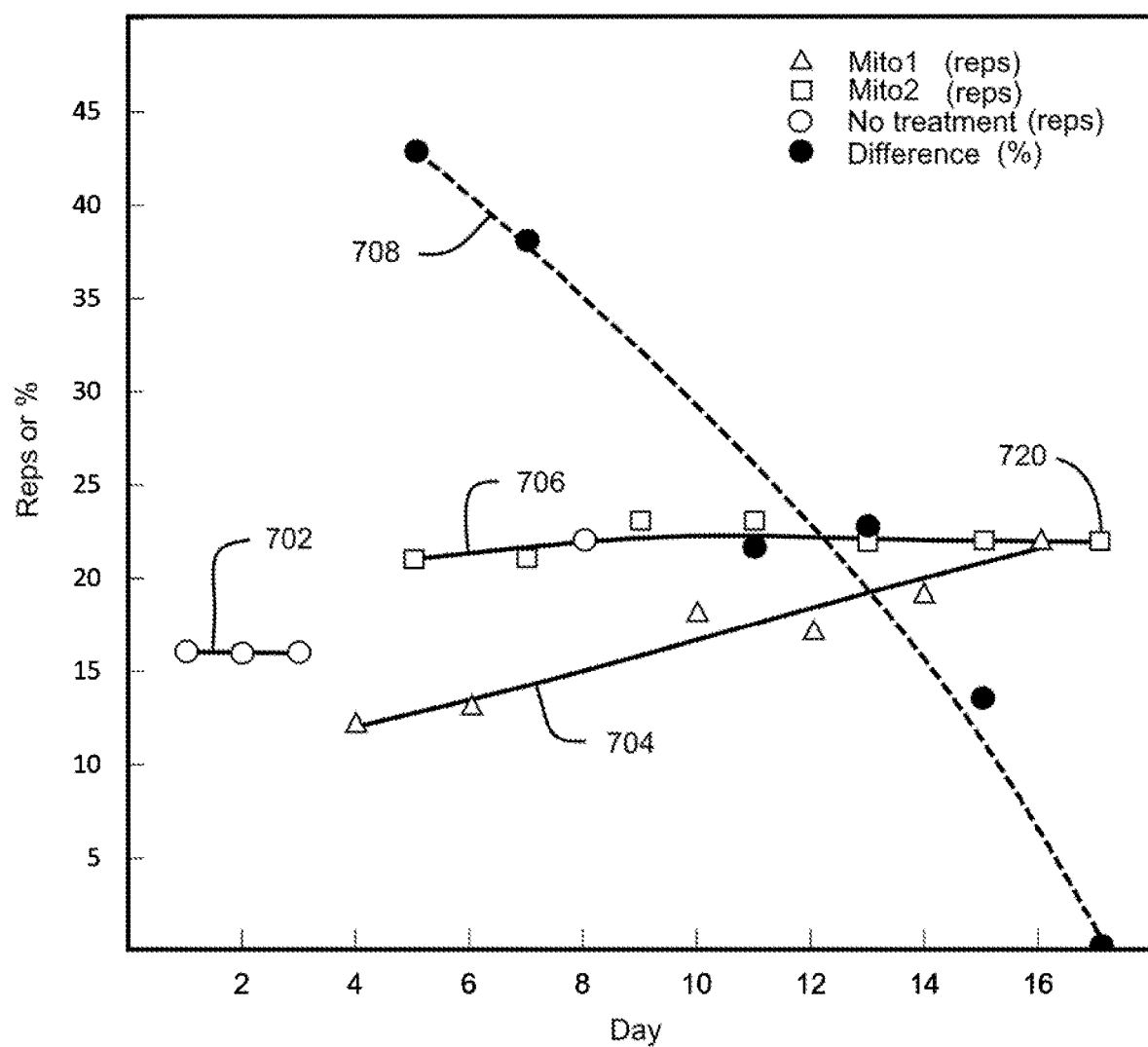
FIG. 7 is a chart of the results from a two week trial of a mtDNA cleanup protocol.

The results tabulated in Table 2 are shown graphically in FIG. 7. Curve 702 shows the baseline number of reps to failure prior to treatment. It is expected that mitochondria were initially in an intermediate, dynamic state between fission and fusion, which is the normal state when fission or fusion is not forced. Curve 704 shows the reps to failure under a forced fission condition using cocktail Mito1, and likewise curve 706 shows the reps to failure under a forced fusion condition using cocktail Mito2. Fusion curve 706 is nearly flat. It is expected that ATP output in the fusion state is nearly maximal due to sharing of enzymes between mtDNA loops, whereas the ATP output in the fission state is much reduced in the absence of sharing. With increasing cycles of fission and fusion, the number of defective mtDNA loops was substantially reduced and the level of methylation was decreased, resulting in curve 704 rising and finally intersecting with curve 706. Dashed curve 708 shows the percent difference between the fusion and fission states, going from 43% initially to 0%—a dramatic improvement after just two weeks. This is much faster than with fission and fusion alone, which would not have substantially eliminated methylation and therefore not taken Δ% to zero.

Mito1 was alternated with Mito2 eleven times, but the number required will be sensitive to the initial level of damage. After point 720, the maximal output was maintained without forcing fusion, and the overall improvement over baseline endurance was 37.5% without any additional fusion supplements. Long term fusion is not desirable as it disables cellular quality control that requires fission and will result in the build-up of mutations. In any case, the accumulation of damage can be expected to occur once again, therefore maintenance protocol MITO3 may be used. MITO3 combines promoters of mitochondrial biogenesis and demethylase, preferably in a unit dose, allowing the natural cycling of mitochondrial morphology to supply the fission and fusion. Mito3 may also be used as an initial treatment, although with substantially slower and perhaps incomplete results.

It is herein hypothesized that mtDNA methylation damage builds up throughout life, playing a major role in age-related obesity and hypertension, and contributing to many other diseases of aging. By alternating cocktails Mito1 and Mito2, it was hypothesized that Δ% should drop rapidly if mitochondrial damage from both major sources were reduced, which indeed occurred during this trial as shown. In addition to gains in endurance, the subject noted a reduction of hunger and a partial resolving of his long standing hypertension. He was able to cut his hypertension medication by half, and found losing weight much easier than before.

PREFERRED DOSES

The following are therapeutically effective doses in mg/kg of an organism for the above cocktails and protocols. Doses are based on an 80 kg subject.

ALA—0.5-100 mg/kg, preferably 1-50 mg/kg, and most preferably 2-30 mg/kg

AKG—0.5-1000 mg/kg, preferably 1-500 mg/kg, and most preferably 2-200 mg/kg

Apigenin—1-100 mg/kg, preferably 2-75 mg/kg, and most preferably 5-50 mg/kg

Azithromycin—0.5-30 mg/kg, preferably 1-20 mg/kg, and most preferably 2-10 mg/kg β-GPA—1-200 mg/kg, preferably 2-50 mg/kg, and most preferably 5-20 mg/kg C60—0.001-1 mg/kg, preferably 0.005-0.1 mg/kg, and most preferably 0.01-0.5 mg/kg GMS—1-250 mg/kg, preferably 5-100 mg/kg, and most preferably 10-30 mg/kg Curcumin—1-250 mg/kg, preferably 5-100 mg/kg, and most preferably 10-50 mg/kg Dasatinib—0.1-4 mg/kg, preferably 0.2-3 mg/kg, and most preferably 0.5-2 mg/kg Dihydromyricetin—0.2-500 mg/kg, preferably 0.5-200 mg/kg, and most preferably 1-100 mg/kg Fisetin—1-500 mg/kg, preferably 2-200 mg/kg, and most preferably 4-100 mg/kg GMS—0.5-200 mg/kg, preferably 1-100 mg/kg, and most preferably 2-50 mg/kg Leucine—5-500 mg/kg, preferably 10-100 mg/kg, and most preferably 20-50 mg/kg Lysine—5-500 mg/kg, preferably 10-100 mg/kg, and most preferably 20-50 mg/kg Metathione—1-200 mg/kg, preferably 2-50 mg/kg, and most preferably 5-20 mg/kg Methylene blue—0.01-20 mg/kg, preferably 0.02-5 mg/kg, and most preferably 0.03-2 mg/kg Myrosinase—0.02 pg/kg-0.02 µg/kg, preferably 1.0 pg/kg-7 ng/kg, and most preferably 0.02-2 ng/kg Navitoclax—0.1-50 mg/kg, preferably 0.5-30 mg/kg, and most preferably 1-20 mg/kg Nicotinic acid, nicotinamide, or combination—0.5-200 mg/kg, preferably 1-50 mg/kg, and most preferably 2-40 mg/kg NMN—1-200 mg/kg, preferably 2-50 mg/kg, and most preferably 5-20 mg/kg Piperlongumine—0.01-0.5 mg/kg, preferably 0.02-0.2 mg/kg, and most preferably 0.03-0.1 mg/kg PQQ—0.01-20 mg/kg, preferably 0.03-10 mg/kg, and most preferably 0.05-5 mg/kg Quercetin—1-100 mg/kg, preferably 1.5-75 mg/kg, and most preferably 2-5 mg/kg Resveratrol—0.01-20 mg/kg, preferably 0.05-10 mg/kg, and most preferably 0.1-5 mg/kg Ribose—1-400 mg/kg, preferably 2-300 mg/kg, and most preferably 4-250 mg/kg Roxithromycin—0.01-5 mg/kg, preferably 0.5-4 mg/kg, and most preferably 1-3 mg/kg SAMe—0.01-50 mg/kg, preferably 0.04-20 mg/kg, and most preferably 0.05-5 mg/kg Sodium and potassium stearates—50 mg to 1 g/kg, preferably 75-750 mg/kg, and most preferably 100-500 mg/kg Stearic acid (except GMS and alkali stearates)—5-800 mg/kg, preferably 10-300 mg/kg, and most preferably 20-200 mg/kg Sulforaphane—0.1-20 mg/kg, preferably 0.5-10 mg/kg, and most preferably 1-5 mg/kg Sulforaphane glucosinolate—0.3-50 mg/kg, preferably 1-25 mg/kg, and most preferably 3-15 mg/kg Taurine—5 mg/kg to 1 g/kg, preferably 10-500 mg/kg, and most preferably 20 to 200 mg/kg Threonine—1-800 mg/kg, preferably 2-300 mg/kg, and most preferably 5-200 mg/kg Tryptophan—1-100 mg/kg, preferably 2-75 mg/kg, and most preferably 5-50 mg/kg

CONCLUSION

Aging is herein seen as an extended Hayflick crisis that can be treated by a protocol comprising activation of mitochondrial switches to replenish stem cell pools, reducing the average epigenetic age of their resident tissues and the organism systemically, thus restoring more youthful function. Epigenetic age can be more rapidly decreased by administering promoters for enzymes to remove aberrant methylation and other epigenetic marks at critical points during the treatment protocol. Mitochondrial dysfunction can be treated by a similar protocol, producing a comprehensive improvement in health and expected longevity.

The section headings used above are for organizational purposes only and are not to be construed as limiting. And although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention as defined in the following claims.

I claim:

1. A method for restoring stem cell pools and reducing epigenetic age of a subject in need thereof, comprising the steps of:
   (a) promoting mitochondrial fusion in the stem cells by administering to the subject therapeutically effective amounts of at least one of the following: stearic acid or source thereof, dihydromyricetin or derivative thereof, sulforaphane or derivative thereof, and fusion promoter M1 (1-(5-Chloro-2-hydroxyphenyl)-ethanone 2-(2,4,6-trichlorophenyl)hydrazone);
   (b) stimulating the fused mitochondria by administering to the subject a therapeutically effective amount of fullerene C60 dissolved in an oil; and
   (c) promoting demethylase by administering to the subject a therapeutically effective amount of alpha-ketoglutarate (AKG) or derivative thereof.

2. A method for restoring stem cell pools and reducing epigenetic age of a subject in need thereof, comprising the steps of:
   (a) promoting mitochondrial fusion in the stem cells by administering to the subject therapeutically effective amounts of each of the following: stearic acid or source thereof, dihydromyricetin or derivative thereof, sulforaphane or derivative thereof, and fusion promoter M1 (1-(5-Chloro-2-hydroxyphenyl)-ethanone 2-(2,4,6-trichlorophenyl)hydrazone);
   (b) stimulating the fused mitochondria by administering to the subject a therapeutically effective amount of fullerene C60 dissolved in an oil; and,
   (c) promoting demethylase by administering to the subject a therapeutically effective amount of alpha-ketoglutarate (AKG) or derivative thereof;
   whereby stem cell pools are at least partially refilled.

3. A method for restoring stem cell pools and reducing epigenetic age of a subject in need thereof, comprising the steps of:
   (a) administering to the subject a therapeutically effective amount of at least one promoter of mitochondrial fusion capable of crossing the blood-brain barrier, selected from the group consisting of dihydromyricetin or derivative thereof, sulforaphane or derivative thereof, and fusion promoter M1 (1-(5-Chloro-2-hydroxyphenyl)-ethanone 2-(2,4,6-trichlorophenyl)hydrazone);
   (b) administering to the subject a therapeutically effective amount of a mitochondrial stimulant comprising fullerene C60 dissolved in an oil; and,
   (c) administering to the subject a therapeutically effective amount of a demethylase promoter comprising alpha-ketoglutarate (AKG) or derivative thereof.

4. The method as recited in claim 3, wherein at least a portion of the fullerene C60 comprises at least one adduct.

5. The method as recited in claim 3, wherein a time interval is provided between steps (a) and (b) to ensure sufficient mitochondrial fusion.

6. The method as recited in claim 3, wherein the at least one promoter of mitochondrial fusion, the fullerene C60 dissolved in an oil, and the promoter of demethylase are provided to the subject for self-administration.

7. A method for restoring stem cell pools and reducing epigenetic age of a subject in need thereof, comprising the steps of:
 (a) administering to the subject at least one promoter of mitochondrial fusion selected from the group consisting of about 100 mg to about 20 g of stearic acid or source thereof, about 20 mg to 40 g dihydromyricetin or derivative thereof, and about 5 mg to about 5 g of sulforaphane or derivative thereof;
 (b) administering to the subject a demethylase promoter comprising about 50 mg to about 50 g of alpha-ketoglutarate (AKG) or derivative thereof; and
 (c) administering to the subject a mitochondrial stimulant comprising about 0.1 mg to about 50 mg of fullerene C60 dissolved in an oil.

8. The method as recited in claim 7, wherein the stearic acid source comprises one or more of the group consisting of monoglycerides, diglycerides and triglycerides comprising stearic acid; and wherein the alpha-ketoglutarate derivative comprises one or more selected from the group consisting of alpha-ketoglutaric acid, ammonium alpha-ketoglutarate, arginine alpha-ketoglutarate, calcium alpha-ketoglutarate, creatine alpha-ketoglutarate, glutamine alpha-ketoglutarate, leucine alpha-ketoglutarate, lithium alpha-ketoglutarate, magnesium alpha-ketoglutarate, ornithine alpha-ketoglutarate, potassium alpha-ketoglutarate, sodium alpha-ketoglutarate, and taurine alpha-ketoglutarate.

9. The method as recited in claim 7, wherein at least a portion of the fullerene C60 comprises at least one adduct.

10. The method as recited in claim 7, wherein the promoter of mitochondrial fusion, the demethylase promoter, and the fullerene C60 are provided to the subject for self-administration.

11. The method as recited in claim 1, further comprising the steps of:
 (d) allowing a time interval after step (c) for stem cell maturation; and
 (e) endogenously promoting mitochondria of the subject to a fission state.

12. The method as recited in claim 11, further comprising the step of:
 (f) administering to the subject a therapeutically effective amount of at least one senolytic agent.

13. The method as recited in claim 12, wherein the senolytic agent is selected from the group consisting of dasatinib, quercetin, navitoclax, piperlongumine, butyrate, fisetin, curcumin and curcumin analogues.

14. The method as recited in claim 3, further comprising the steps of:
 (d) allowing a time interval after step (c) for stem cell maturation; and
 (e) endogenously promoting mitochondria of the subject to a fission state.

15. The method as recited in claim 14, further comprising the step of:
 (f) administering to the subject a therapeutically effective amount of at least one senolytic agent.

16. The method as recited in claim 15, wherein the senolytic agent is selected from the group consisting of dasatinib, quercetin, navitoclax, piperlongumine, butyrate, fisetin, curcumin and curcumin analogues.

17. The method as recited in claim 1, wherein the alpha-ketoglutarate derivative comprises one or more selected from the group consisting of alpha-ketoglutaric acid, ammonium alpha-ketoglutarate, arginine alpha-ketoglutarate, calcium alpha-ketoglutarate, creatine alpha-ketoglutarate, glutamine alpha-ketoglutarate, leucine alpha-ketoglutarate, lithium alpha-ketoglutarate, magnesium alpha-ketoglutarate, ornithine alpha-ketoglutarate, potassium alpha-ketoglutarate, sodium alpha-ketoglutarate, and taurine alpha-ketoglutarate.

18. The method as recited in claim 2, wherein the alpha-ketoglutarate derivative comprises one or more selected from the group consisting of alpha-ketoglutaric acid, ammonium alpha-ketoglutarate, arginine alpha-ketoglutarate, calcium alpha-ketoglutarate, creatine alpha-ketoglutarate, glutamine alpha-ketoglutarate, leucine alpha-ketoglutarate, lithium alpha-ketoglutarate, magnesium alpha-ketoglutarate, ornithine alpha-ketoglutarate, potassium alpha-ketoglutarate, sodium alpha-ketoglutarate, and taurine alpha-ketoglutarate.

19. The method as recited in claim 3, wherein the alpha-ketoglutarate derivative comprises one or more selected from the group consisting of alpha-ketoglutaric acid, ammonium alpha-ketoglutarate, arginine alpha-ketoglutarate, calcium alpha-ketoglutarate, creatine alpha-ketoglutarate, glutamine alpha-ketoglutarate, leucine alpha-ketoglutarate, lithium alpha-ketoglutarate, magnesium alpha-ketoglutarate, ornithine alpha-ketoglutarate, potassium alpha-ketoglutarate, sodium alpha-ketoglutarate, and taurine alpha-ketoglutarate.

20. The method as recited in claim 1, wherein at least a portion of the fullerene C60 comprises at least one adduct.

\* \* \* \* \*